(12) United States Patent
Myoujou et al.

(10) Patent No.: US 8,626,453 B2
(45) Date of Patent: Jan. 7, 2014

(54) BLOOD GLUCOSE LEVEL INFORMATION PROCESSING APPARATUS, BLOOD GLUCOSE LEVEL INFORMATION PROCESSING METHOD AND BLOOD GLUCOSE LEVEL INFORMATION PROCESSING PROGRAM

(75) Inventors: Hiroyuki Myoujou, Ashigarakami-gun (JP); Tooru Oomori, Chiyoda-ku (JP); Jun Tsubota, Chiyoda-ku (JP)

(73) Assignee: Terumo Kabushiki Kaisha, Tokyo (JP)

( * ) Notice: Subject to any disclaimer, the term of this patent is extended or adjusted under 35 U.S.C. 154(b) by 208 days.

(21) Appl. No.: 13/074,409

(22) Filed: Mar. 29, 2011

(65) Prior Publication Data

US 2011/0196217 A1     Aug. 11, 2011

Related U.S. Application Data

(63) Continuation of application No. PCT/JP2009/066707, filed on Sep. 16, 2009.

(30) Foreign Application Priority Data

Sep. 29, 2008  (JP) .................................. 2008-251767
Sep. 29, 2008  (JP) .................................. 2008-251768

(51) Int. Cl.
    *A61B 5/145*       (2006.01)
(52) U.S. Cl.
    USPC .................. 702/31; 700/17; 700/18; 700/83; 700/266; 702/19; 702/22; 702/32; 600/365
(58) Field of Classification Search
    USPC .................. 700/266, 17, 18, 83, 19; 600/365; 702/19, 22, 31, 32
    See application file for complete search history.

(56) References Cited

U.S. PATENT DOCUMENTS

| 5,345,550 | A | * | 9/1994 | Bloomfield .................. 715/841 |
| 2007/0033074 | A1 | | 2/2007 | Nitzan et al. |
| 2008/0235053 | A1 | | 9/2008 | Ray et al. |

FOREIGN PATENT DOCUMENTS

JP            63-135144 A      6/1988
(Continued)

OTHER PUBLICATIONS

English translation of Chinese Office Action issued Jul. 17, 2012 by The State Intellectual Property Office of P.R. China in corresponding Chinese Application No. 200980138544.1.

(Continued)

*Primary Examiner* — Brian R Gordon
*Assistant Examiner* — Shogo Sasaki
(74) *Attorney, Agent, or Firm* — Buchanan Ingersoll & Rooney PC

(57) ABSTRACT

A blood glucose level information processing apparatus, method and program provide blood glucose values and blood glucose value information within a period or range desired by a user without imposing cumbersome operation on the user. The apparatus, method and program provide blood glucose values and blood glucose value information within a period or desired range by acquiring blood glucose levels measured by a blood glucose level measuring device and date/time of measurement at which the blood glucose levels are measured, displaying a line graph obtained by plotting the blood glucose values within a predetermined period. A slide bar can also be provided, for example on a graph display screen image, whereupon if the slide bar is moved, only the blood glucose values corresponding to a preceding period backdating in response to the amount of movement of the slide bar are plotted on a line graph along a time series.

7 Claims, 29 Drawing Sheets

(56) References Cited

FOREIGN PATENT DOCUMENTS

| | | |
|---|---|---|
| JP | 2000-060803 A | 2/2000 |
| JP | 2001-245900 A | 9/2001 |
| JP | 2003-271737 A | 9/2003 |
| JP | 2008-191716 A | 8/2008 |
| WO | 2004 023972 A2 | 3/2004 |

OTHER PUBLICATIONS

International Search Report (PCT/ISA/210) issued on Dec. 22, 2009, by Japanese Patent Office as the International Searching Authority for International Application No. PCT/JP2009/066707.

Extended European Search Report issued on Feb. 9, 2012, by European Patent Office in corresponding European Patent Application No. 09816225.8—2404/ 2333527. (5 pages).

* cited by examiner

| TIME SLOT | SET INPUT TIME | MEASUREMENT TIME |
|---|---|---|
| BEFORE BREAKFAST | 03:00 | 03:00~07:00 |
| AFTER BREAKFAST | 07:00 | 07:00~10:00 |
| BEFORE LUNCH | 10:00 | 10:00~12:00 |
| AFTER LUNCH | 12:00 | 12:00~15:00 |
| BEFORE SUPPER | 15:00 | 15:00~18:00 |
| AFTER SUPPER | 18:00 | 18:00~21:00 |
| BEFORE GOING TO BED | 21:00 | 21:00~24:00 |
| LATE AT NIGHT | 24:00 | 24:00~03:00 |

FIG.13

BLOOD GLUCOSE LEVEL INFORMATION PROCESSING APPARATUS, BLOOD GLUCOSE LEVEL INFORMATION PROCESSING METHOD AND BLOOD GLUCOSE LEVEL INFORMATION PROCESSING PROGRAM

This application is a continuation of International Application No. PCT/JP2009/066707 filed on Sep. 16, 2009, and claims priority to Japanese Application No. 2008-251767 filed on Sep. 29, 2008 and Japanese Application No. 2008-251768 filed on Sep. 29, 2008, the entire content of all three of which is incorporated herein by reference.

TECHNICAL FIELD

This invention generally pertains to the measurement of glucose level in blood. More specifically, the invention relates to a blood glucose level information processing apparatus, a blood glucose level information processing method and a blood glucose level information processing program. The apparatus, method and program can be used, for example, in a situation in which the transition of the blood glucose level measured periodically by an external blood glucose level measuring instrument is represented by and provided as a graph.

BACKGROUND DISCUSSION

Nowadays, it is reported that the number of diabetics all over Japan amounts to approximately 6,000,000. Among them, approximately 2,000,000 diabetics go to hospital regularly as outpatients while the others are potential patients. Therapy for such diabetics includes alimentary therapy, ergotherapy, pharmacotherapy, insulin therapy and so forth. Whichever therapy is applied, daily blood glucose level management of each patient is very significant.

However, even in the case where a patient himself/herself uses a blood glucose level measuring instrument to periodically measure the blood glucose level, it may not be easy to grasp the transition of the blood glucose level with respect to time and blood glucose level information such as a maximum value, a minimum value and a mean value of the blood glucose level. Many patients feel happy and anxious in turn with a variation of the measured blood glucose level, but cannot necessarily recognize accurately in what manner the variation of the blood glucose level is associated with the patient's way of living, the amount of a food ingested, the time zone and so forth.

Further, while the number of doctors as specialists for diabetes is approximately 10,000 over Japan, the number of diabetics is approximately 6,000,000 as described above. Therefore, one doctor must examine 600 patients. Further, since it is estimated that there is a tendency that diabetics increase in the future, a blood glucose level information processing apparatus is demanded which allows the blood glucose level to be periodically measured by the patient to be managed readily and allows a doctor to relatively easily handle the transition of the blood glucose level with respect to time and the blood glucose level information and make a diagnosis appropriately.

According to one of such blood glucose level information processing apparatus as just described, a blood glucose level measured by a blood glucose level measuring instrument and the date/time of the measurement at which the blood glucose level is measured are acquired, and the blood glucose level is classified based on the date/time of the measurement into one of several time slots, namely "before breakfast," "after breakfast," "before lunch," "after lunch," "before supper," "after supper," "before going to bed," "late at night" and so forth. An example of such an apparatus is described in Japanese Patent Laid-Open No. 2000-60803.

Consequently, the blood glucose level information processing apparatus can provide blood glucose levels and blood glucose level information based on the blood glucose levels statistically to a doctor and so forth for the individual time slots. Further, by displaying the blood glucose levels and the blood glucose level information based on the blood glucose levels as a graph along a time series based on the date/time of the measurement, the blood glucose level information processing apparatus allows a doctor or the like to easily grasp a tendency of the blood glucose levels and the blood glucose level information.

The conventional blood glucose level information processing apparatus has a problem in that, when blood glucose levels and blood glucose level information are displayed as a graph along a time series based on the date/time of measurement, the time axis cannot be varied readily, and therefore, cumbersome operation is imposed on a user when blood glucose levels and blood glucose level information within a period or range desired by the user are to be provided readily.

Further, in a conventional blood glucose level information processing apparatus, when a blood glucose value is to be sorted into one of time slots, it is sorted based on the date/time of measurement. Therefore, when actual meal time is different from the set time, the blood glucose level cannot be sorted appropriately. Accordingly, there is a problem that an accurate blood glucose value and accurate blood glucose value information for each time slot cannot be provided.

SUMMARY

According to one aspect, a blood glucose level information processing apparatus comprises acquisition means for acquiring blood glucose levels measured by an external blood glucose level measuring instrument and for acquiring a measurement date and a measurement time at which each of the blood glucose levels is measured; and display control means for controlling a display to display a blood glucose level graph which plots the acquired blood glucose levels measured during a first range of measurement dates and at least during one of the measurement times, and to also display a bar which is operable to select a second range of measurement dates different from the first range of measurement dates. The display control means controls the display to display a different blood glucose level graph, plotting the acquired blood glucose levels measured during the second range of measurement dates and at least during the one measurement time, if the bar is operated, wherein the first range of measurement dates and the second range of measurement dates contain a common number of the measurement dates so that the blood glucose level graph which plots the acquired blood glucose levels measured during the first range of measurement dates and the different blood glucose level graph which plots the acquired blood glucose levels measured during the second range of measurement dates both plot the acquired blood glucose levels measured during the same number of days.

By simply operating the bar (e.g., moving a slide bar according to the embodiment disclosed as an example), a blood glucose level graph obtained by plotting the blood glucose levels corresponding to the preceding period in response to the amount of movement of the slide bar can be displayed. Thus, the blood glucose levels and the blood glucose level information within the period or range desired by a user can be provided readily without imposing cumbersome operation on the user.

According to another aspect, a blood glucose level information processing method involves: acquiring blood glucose levels, a measurement date at which each blood glucose level is measured, and a measurement time at which each blood glucose level is measured; displaying a blood glucose level graph which plots the acquired blood glucose levels measured during a first range of measurement dates and at least during one of the measurement times, and to also display a bar which is operable to select a second range of measurement dates different from the first range of measurement dates; and when the bar is operated, changing the display to display the blood glucose level graph for a second range of measurement dates and at least during the one measurement time, with the first range of measurement dates and the second range of measurement dates containing a common number of the measurement dates so that the blood glucose level graph plotting the acquired blood glucose levels measured during the first range of measurement dates and the blood glucose level graph which plots the acquired blood glucose levels measured during the second range of measurement dates both plot the acquired blood glucose levels measured over the same number of days.

Also disclosed is a blood glucose level information processing program stored in a non-transitory computer readable medium to cause a computer to: acquire measured blood glucose levels, together with measurement dates and measurement times at which each of the blood glucose levels is measured; and display a first blood glucose level graph plotting the acquired blood glucose levels measured during a first range of measurement dates and at least during one of the measurement times, while also displaying a bar which is operable to select a second range of measurement dates different from the first range of measurement dates. The program also causes the computer to change the display upon operation of the bar to display a second blood glucose level graph plotting the acquired blood glucose levels measured during the second range of measurement dates and at least during the one measurement time, the first and second blood glucose level graphs plotting the acquired blood glucose levels over the same number of measurement dates.

Another aspect of the disclosure here involves a blood glucose level information processing apparatus comprising: acquisition means for acquiring blood glucose levels measured by an external blood glucose level measuring instrument and to acquire measurement dates and measurement times at which the blood glucose levels are measured; sorting means for sorting the measured blood glucose levels acquired by the acquisition means into a plurality of time slots based on the acquired measurement dates and measurement times, each time slot encompassing a predetermined time period; and display control means for controlling a display unit to display at least some of the acquired blood glucose levels in a table having one axis representing dates and another axis representing the plural time slots and to display, upon selecting one of the blood glucose values in a current time slot within the table, a popup menu having one button selectable to direct the selected blood glucose value to be moved from the current time slot to a different time slot preceding the current time slot and an other button selectable to direct the selected blood glucose value to be moved a different time slot succeeding the current time slot. A changing means changes the selected blood glucose level to the preceding time slot when the one button of the pop-up menu is selected and for changing the selected blood glucose level to the succeeding time slot when the other button of the pop-up menu is selected.

If an arbitrary blood glucose level is selected from among the blood glucose levels displayed in a table, the popup menu is displayed, and by simply selecting the forward button or the rearward button of the popup menu, the time slot of the arbitrary blood glucose level can be changed. Thus, a more accurate blood glucose level and more accurate blood glucose level information than ever can be provided.

A blood glucose level information processing method includes: acquiring blood glucose levels as well as a measurement date and a measurement time at which each blood glucose level was measured; sorting the acquired blood glucose levels into a plurality of respective time slots which each include a respective period of time so that acquired blood glucose levels measured during each respective time period are sorted into the respective time slot; displaying at least some of the acquired blood glucose levels in a table which has one axis representing dates and another axis representing the plural time slots; and displaying a popup menu when one of the blood glucose values displayed in the table in a current time slot is selected, the popup menu including one button selectable to direct the selected blood glucose value to be moved from the current time slot to a different time slot preceding the current time slot and an other button to direct the selected blood glucose value to be moved a different time slot succeeding the current time slot. The method additionally includes moving the selected blood glucose level to the preceding time slot when the one button of the pop-up menu is selected and moving the selected blood glucose level to the succeeding time slot when the other button of the pop-up menu is selected.

An additional aspect disclosed here involves a blood glucose level information processing program stored in a non-transitory computer readable medium to cause a computer to: acquire blood glucose levels as well as a measurement date and a measurement time at which each blood glucose level was measured; sort the acquired blood glucose levels into a plurality of respective time slots which each include a respective period of time so that acquired blood glucose levels measured during each respective time period are sorted into the respective time slot; display at least some of the acquired blood glucose levels in a table which has one axis representing dates and another axis representing the plural time slots; display a popup menu when one of the blood glucose values displayed in the table in a current time slot is selected, the popup menu including one button selectable to direct the selected blood glucose value to be moved from the current time slot to a different time slot preceding the current time slot and an other button to direct the selected blood glucose value to be moved a different time slot succeeding the current time slot; and move the selected blood glucose level to the preceding time slot when the one button of the pop-up menu is selected and moving the selected blood glucose level to the succeeding time slot when the other button of the pop-up menu is selected.

BRIEF DESCRIPTION OF THE DRAWINGS

FIG. 7 is a schematic illustration of a configuration of a time slot table.

FIG. 13 is a schematic illustration of a configuration of a graph display screen image in which an average graph and a standard deviation line graph of monthly averages are displayed.

DETAILED DESCRIPTION (1) Configuration of the Blood Glucose Level Information Processing System FIG. 1 illustrates a blood glucose level information processing system 1 according to one embodiment disclosed here by way of example. The blood glucose level information processing system 1 includes a blood glucose level information processing apparatus 2, a printer 3 and a blood glucose level measuring unit 4.

Figure 1:
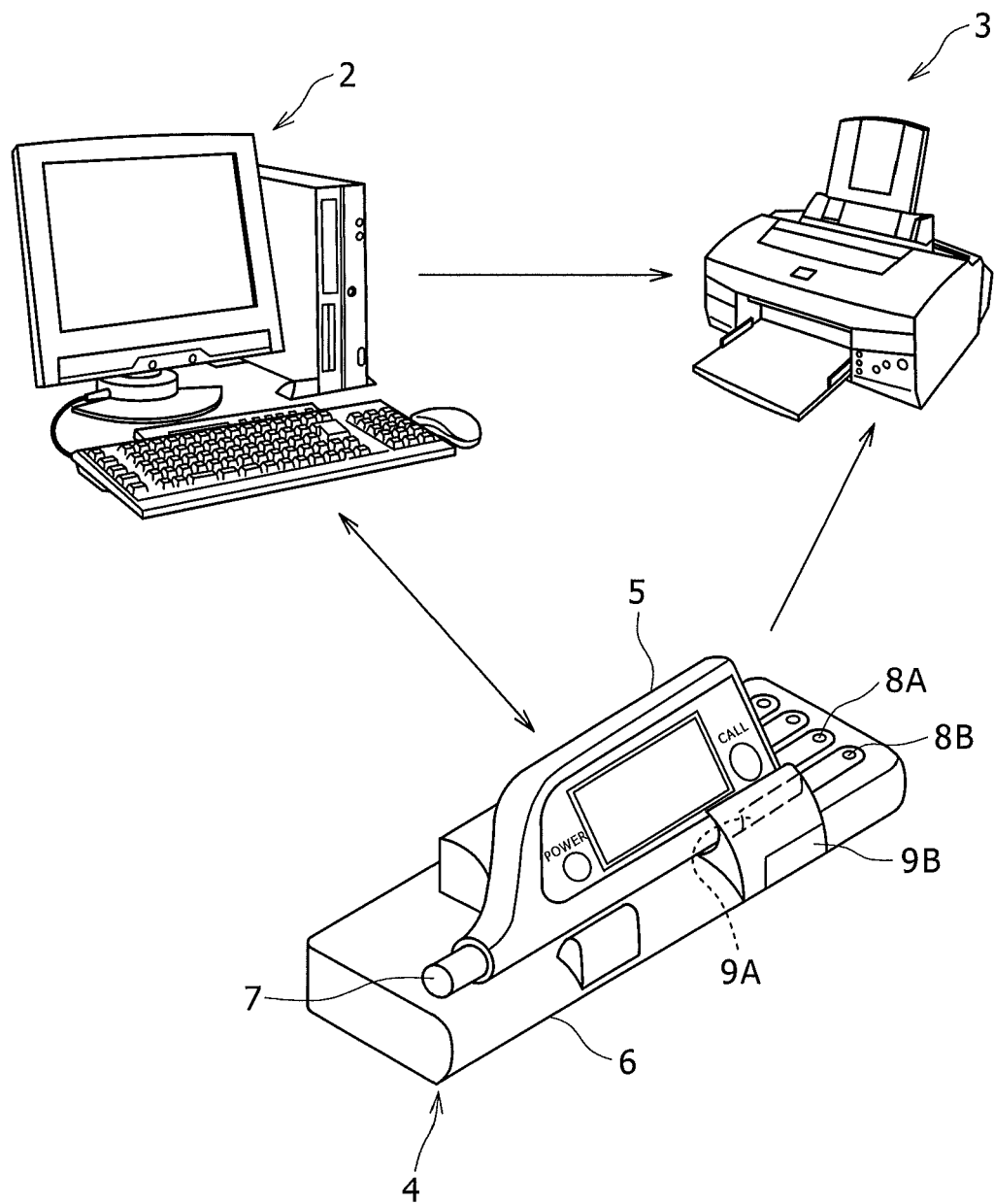
FIG. 1 is a schematic view of a blood glucose level information processing apparatus.

The blood glucose level information processing apparatus 2 is comprised of, for example, from a personal computer and is connected to the printer 3, for example, by a USB (Universal Serial bus) cable. Further, the blood glucose level information processing apparatus 2 is configured such that it can carry out optical communication with the blood glucose level measuring unit 4 through an optical communication module (not shown) connected by an RS232C cable.

The blood glucose level measuring unit 4 includes a blood glucose level measuring device 5 for allowing a patient to measure the blood glucose level, and a communication module 6 for communicating with the blood glucose level information processing apparatus 2 and the printer 3.

The blood glucose level measuring device 5 samples the blood of a patient by means of an exchangeable measuring tip 7 provided at an end thereof, causes the sampled blood and a reagent enclosed in the measuring tip 7 to react with each other and optically reads the color of the blood after the reaction to measure the concentration of glucose in the blood to obtain a blood glucose level as a result of the measurement.

Further, the blood glucose level measuring device 5 has a clock function in the inside thereof and counts the time based on the date/time inputted by a user, for example, upon initialization. The blood glucose level measuring device 5 stores a blood glucose level measured thereby as measurement data, for example, into a nonvolatile memory provided in the inside of the blood glucose level measuring device 5 itself together with the date/time of the measurement.

Here, since the blood glucose level varies when the patient east (e.g., at the time of a mea) and depending upon the time of day (time slot) and the way of living, in order to grasp the variation, a patient will carry out measurement of the blood glucose level plural times each day such as, for example, before breakfast, after breakfast, before lunch, after lunch, before supper, after supper, before going to bed and late at night using the blood glucose level measuring device 5.

The blood glucose level measuring device 5 is configured such that it can store measurement data, for example, for 150 times of measurement. If the patient measures blood glucose level, for example, four times a day, then the blood glucose level measuring device 5 can store measurement data for approximately 36 days.

The blood glucose level measuring device 5 includes an optical communication transmission/reception unit at a position opposing an optical communication transmission/reception unit 9A of the communication module 6 and can optically communicate with the communication module 6.

If an optical communication button 8A on the blood glucose level measuring unit 4 is operated or depressed by the user in a state in which the blood glucose level measuring device 5 is placed on the communication module 6, the communication module 6 causes the blood glucose level measuring device 5 to transmit measurement data stored in the memory of the blood glucose level measuring device 5 through the optical communication transmission/reception unit. The communication module 6 then receives the measurement data by optical communication through the optical communication transmission/reception unit 9A.

The communication module 6 then transmits the measurement data received from the blood glucose level measuring device 5 to the blood glucose level information processing apparatus 2 through another optical communication transmission/reception unit 9B.

If a print button 8B is operated or depressed by the user in the state in which the blood glucose level measuring device 5 is placed on the communication module 6, the communication module 6 receives measurement data from the blood glucose level measuring device 5 similarly as in the case in which the optical communication button 8A is operated or depressed.

Then, the communication module 6 transmits the measurement data to the printer 3 to which the communication module 6 is connected by a cable so that the blood glucose levels and the date/time of the measurements of the measurement data can be printed in an order beginning with the older date of time of measurement by the printer 3.

Figure 2:
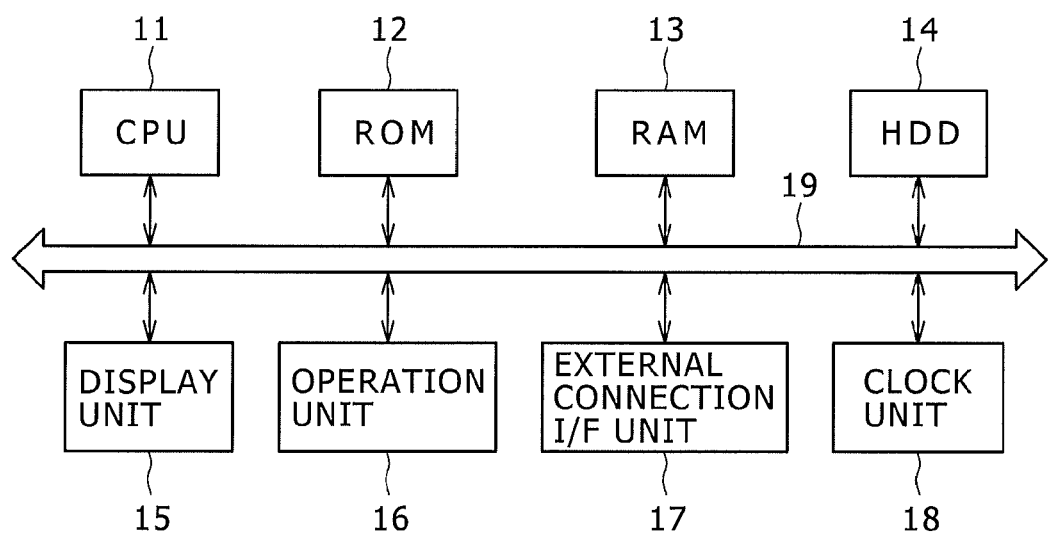
FIG. 2 is a schematic illustration of a circuit configuration of the blood glucose level information processing apparatus.

(2) Circuit Configuration of the Blood Glucose Level Information Processing Apparatus As shown in FIG. 2, the blood glucose level information processing apparatus 2 includes a CPU (Central Processing Unit) 11, a ROM (Read Only Memory) 12, a RAM (Random Access Memory) 13, a hard disk drive 14, a display unit 15 in the form of an LCD (Liquid Crystal Display) unit or the like, an operation unit 16 including a mouse, a keyboard and so forth, an external connection interface unit 17 and a clock unit 18 for counting the time, all connected to each other by a bus 19.

In this blood glucose level information processing apparatus 2, the CPU 11 reads out a basic program stored in the ROM 12 and develops the basic program into the RAM 13, and supervisorily controls the entire blood glucose level information processing apparatus 2 in accordance with the basic program. Further, the blood glucose level information processing apparatus 2 develops various application programs stored in the ROM 12 or the hard disk drive 14 into the RAM 13 and executes various processes in accordance with the various application programs.

The blood glucose level information processing apparatus 2 is connected to an optical communication module (not shown) through an RS232C cable connected to the external connection interface unit 17 and connected to the printer 3 (FIG. 1) through a USB cable connected to the external connection interface unit 17.

Accordingly, if the optical communication button 8A of the communication module 6 is operated or depressed by the user and measurement data are transmitted from the blood glucose level measuring device 5 to the blood glucose level information processing apparatus 2 through the communication module 6, then the blood glucose level information processing apparatus 2 receives the measurement data through the external connection interface unit 17 and stores the measurement data into the hard disk drive 14.

At this time, since it is expected that the blood glucose level information processing apparatus 2 receives measurement data from a large number of blood glucose level measuring devices 5, the blood glucose level information processing apparatus 2 stores measurement data into folders provided, for example, in the hard disk drive 14 and individually associated with different patient names.

(3) Blood Glucose Level Information Process

If the blood glucose level information processing program is selected in response to an operation of the operation unit 16 by a user (in this instance, for example, a doctor), then the CPU 11 reads out the blood glucose level information processing program from the hard disk drive 14 and develops the blood glucose level information processing program into the RAM 13. Then, the CPU 11 executes the blood glucose level information process in accordance with the blood glucose level information processing program.

Figure 3:
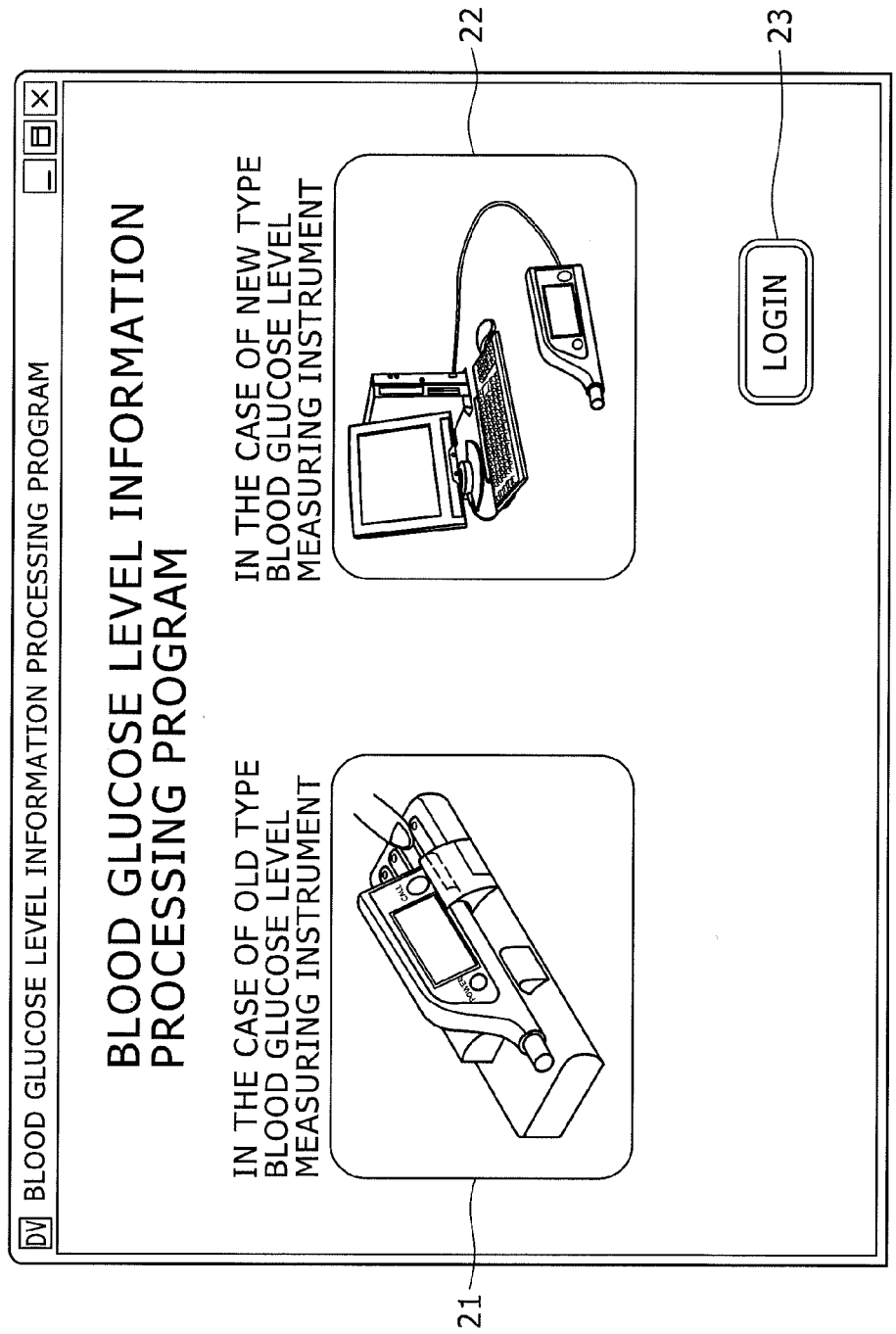
FIG. 3 is a schematic illustration of a configuration of a start screen image.

When the CPU 11 executes the blood glucose level information process, it causes the display unit 15 to display a start screen image 20 as shown in FIG. 3. The start screen image 20 displays blood glucose level measuring device guide illustrations 21 and 22 for guiding transmission methods, for example, for transmission of measurement data from the blood glucose level measuring devices 5 of two different types, and a login button 23 for allowing login of a doctor.

Figure 4:
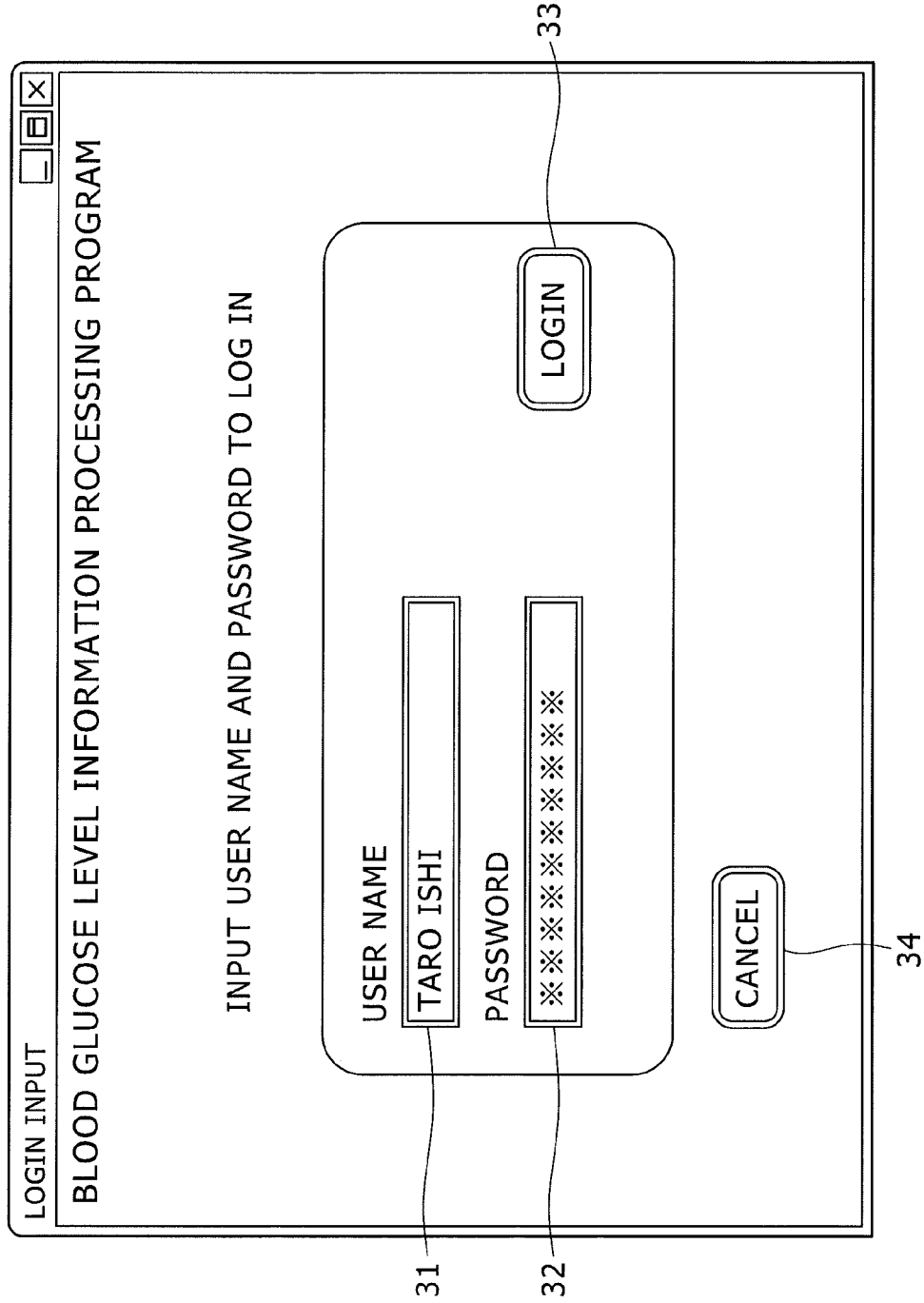
FIG. 4 is a schematic illustration of a configuration of a login screen image.

If the login button 23 of the start screen image 20 is selected, for example, by a cursor in response to an operation of the operation unit 16 by the doctor, then the CPU 11 controls the display unit 15 to display a login screen image 30 for requesting the doctor to login as shown in FIG. 4. This login screen image 30 displays a user name input field 31 and a password input field 32 into which a user name and a password are to be inputted, respectively, a login button 33 for allowing the user to carry out login, and a cancel button 34 for canceling the login procedure.

Figure 5:
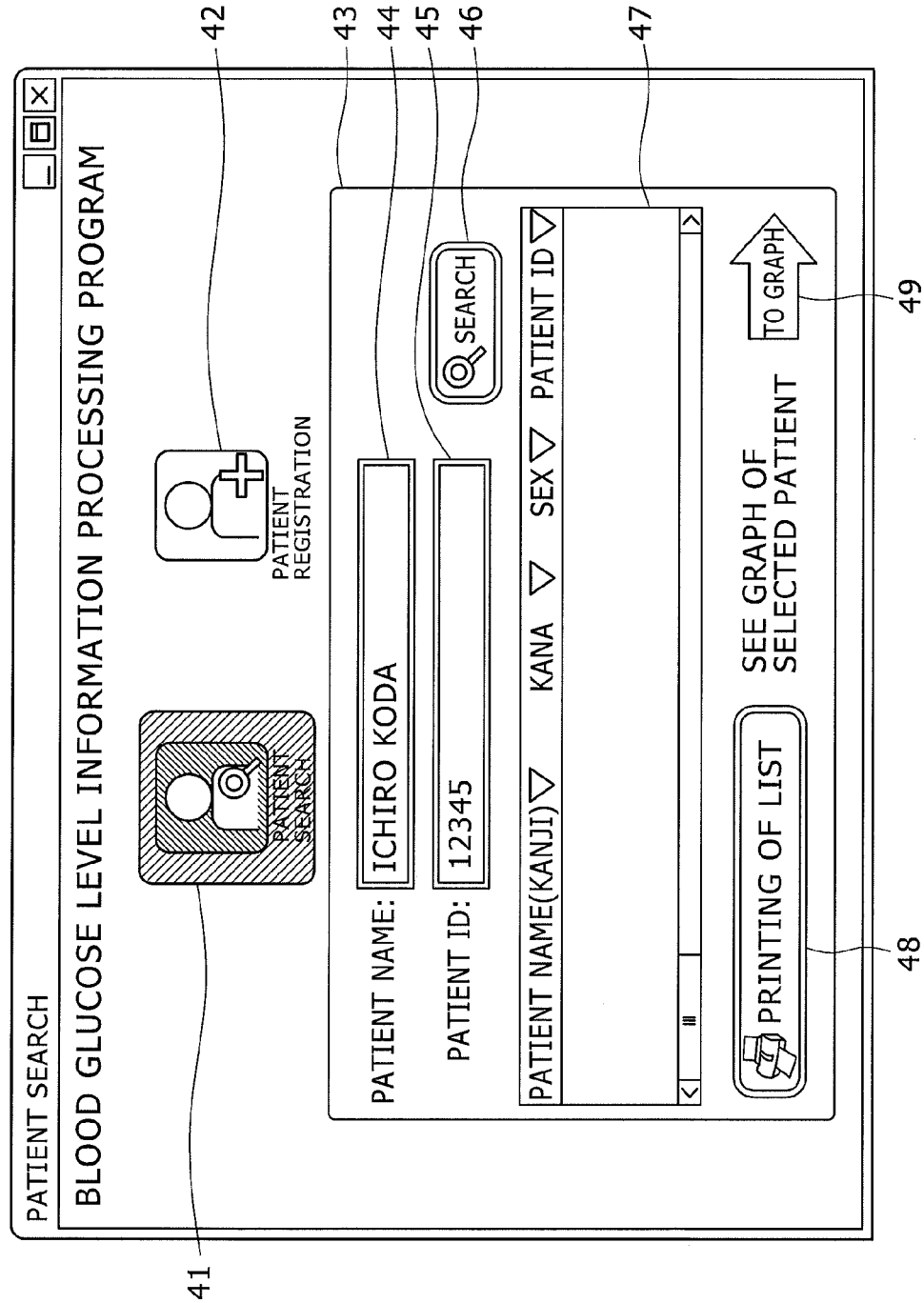
FIG. 5 is a schematic illustration of one configuration of a patient search screen image.

If a user name and a password are inputted to the user name input field 31 and the password input field 32, respectively, in response to an operation of the operation unit 16 by the doctor and then the login button 33 is selected, then the CPU 11 decides whether or not they coincide with a user name and a password registered in advance, respectively. If they coincide with each other, then the CPU 11 controls the display unit 15 to display a patient search screen image 40 as seen in FIG. 5.

The patient search screen image 40 displays a patient search button 41 for selecting a mode (hereinafter referred to as search mode) in which a patient database registered, for example, in advance in the hard disk drive 14 is searched for a particular patient, a patient registration button 42 for selecting another mode (hereinafter referred to as registration mode) in which a new patient is registered into the patient database, and a by-mode display region 43. In the patient database, the name, kana, sex, patient ID and so forth of patients are registered in an associated relationship with each other.

When the patient search screen image 40 is displayed on the display unit 15, the patient search button 41 is selected by default. The CPU 11 causes the display unit 15 to display the patient search screen image 40 such that a patient name input field 44 and a patient ID input field 45 into which a patient name and a patient ID are to be inputted, respectively, a search button 46 for executing a search, a patient list display field 47 for displaying a search result in a list, a print button 48, and a graph display button 49 are displayed in the by-mode display region 43.

Then, at least one of a patient name and a patient ID would be inputted to the patient name input field 44 or the patient ID input field 45 in response to an operation of the operation unit 16 by the doctor, and then the search button 46 would be selected.

Figure 6:
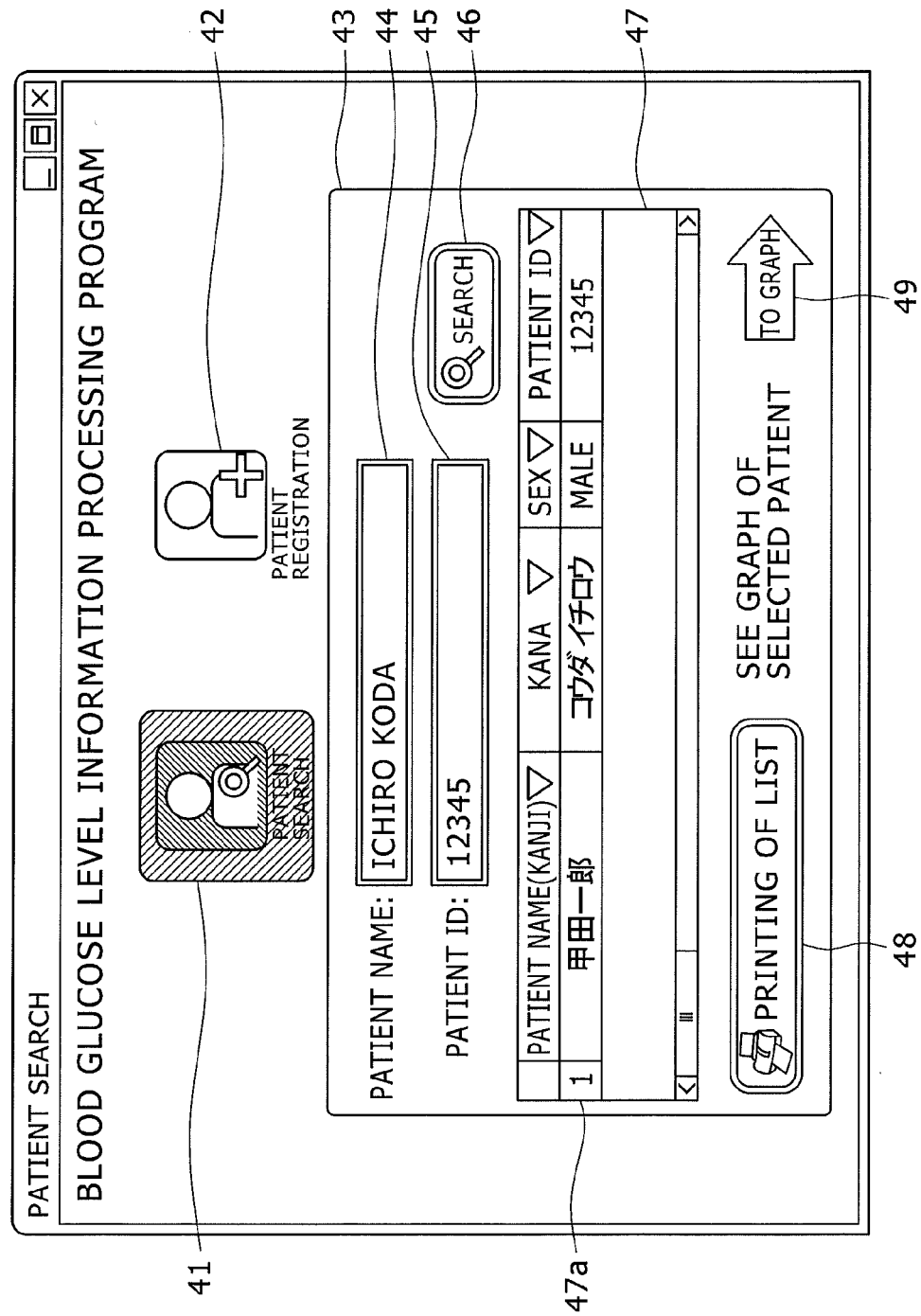
FIG. 6 is a schematic illustration of another configuration of the patient search screen image.

At this time, the CPU 11 searches the patient database stored in the hard disk drive 14 for the patient name and the patient ID inputted to the patient name input field 44 and the patient ID input field 45, respectively. Then, if a coincident patient name or patient ID is detected, then the CPU 11 reads out the name, kana, sex and patient ID of the coincident patient from the patient database and causes the read out information to be displayed as a patient item 47a in the patient list display field 47 as seen in FIG. 6.

If the print button 48 is selected in response to an operation of the operation unit 16 by the doctor in the state in which the patient item 47a is displayed in the patient list display field 47, then the CPU 11 causes the patient list display field 47 to be printed by the printer 3 (FIG. 1) through the external connection interface unit 17.

If the patient registration button 42 of the patient search screen image 40 is selected through the operation unit 16, the CPU 11 executes the registration mode so that a patient can be newly registered.

If the graph display button 49 is selected after the patient item 47a of the patient list display field 47 is selected through the operation unit 16, then the CPU 11 reads out measurement data stored in a folder corresponding to the patient name of the selected patient item 47a from the hard disk drive 14.

Then, the CPU 11 compares the date/time of measurement of the blood glucose level of the read out measurement data with such a time slot table 60 as illustrated in FIG. 7 to sort the blood glucose level into one of the time slots of the time slot table 60.

Here, in the time slot table 60, for example, eight time slots are used including those of "before breakfast," "after breakfast," "before lunch," "after lunch," "before supper," "after supper," "before going to bed" and "late at night."

In the time slot table 60, by inputting predetermined input time through the operation unit 16 in advance, the time slot "before breakfast" corresponds to measurement time "03:00~07:00"; the time slot "after breakfast" to measurement time "07:00~10:00"; the time slot "before lunch" to measurement time "10:00~12:00"; the time slot "after lunch" to measurement time "12:00~15:00"; the time slot "before supper" to measurement time "15:00~18:00"; the time slot "after supper" to measurement time "18:00~21:00"; the time slot "before going to bed" to measurement time "21:00~24:00"; and the time slot "late at night" to measurement time "24:00~03:00."

Accordingly, if the measurement time based on the date/time of measurement of the measurement data read out from the hard disk drive 14 is, for example, "06:30," then the CPU 11 sorts the blood glucose level of the measurement data into the time slot "before breakfast." However, if the measurement time of the measurement data is "14:20," then the CPU 11 sorts the blood glucose level of the measurement data into the time slot "after lunch."

After the CPU 11 reads out the measurement data stored in the folder corresponding to the patient name of the patient item 47a from the hard disk drive 14, the CPU 11 sorts the blood glucose level of each of the read out measurement data into one of the time slots in this manner.

Figure 8:
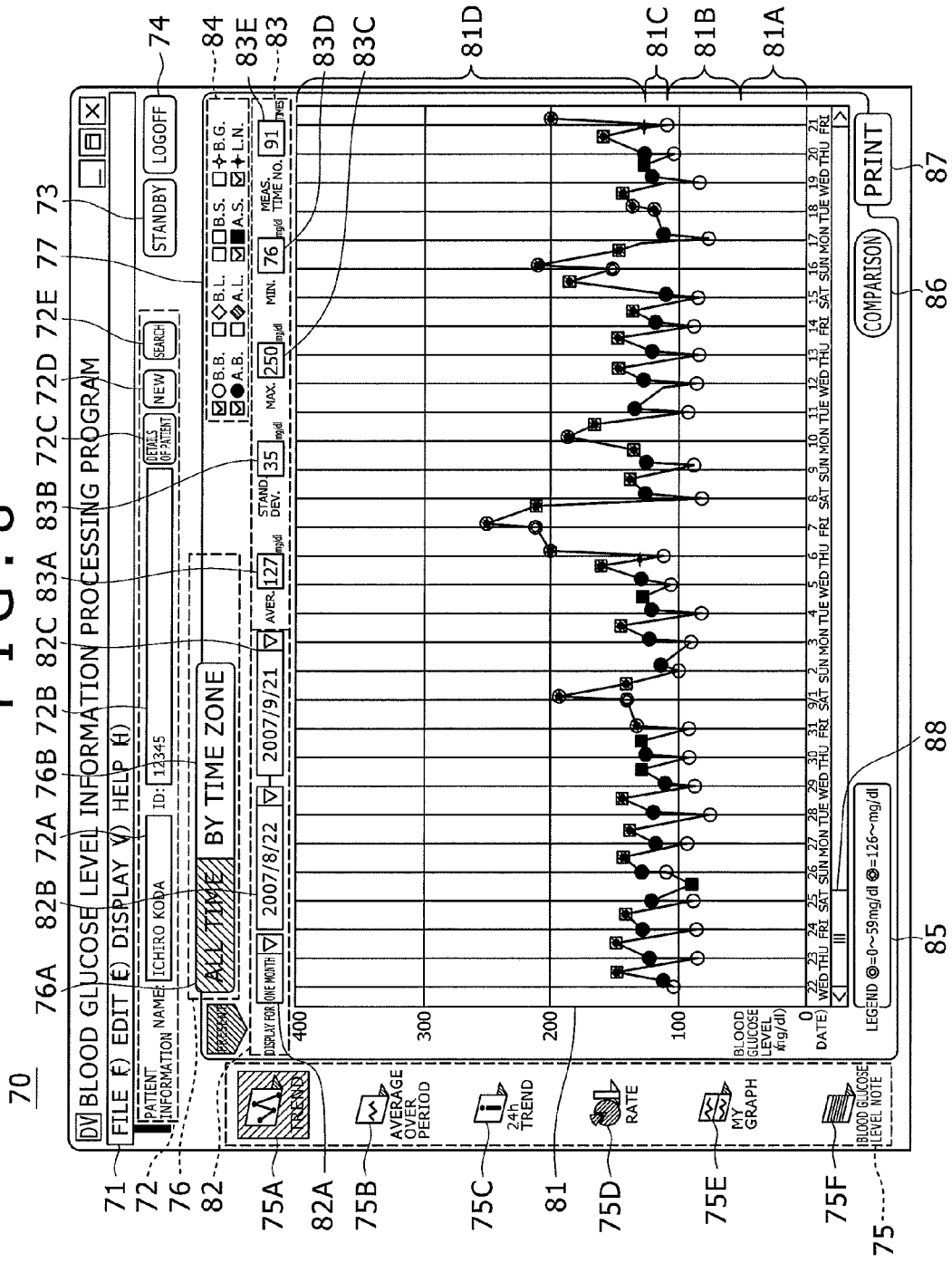
FIG. 8 is a schematic illustration of one configuration of a graph display screen image displaying a line graph over the whole time.

Then, the CPU 11 produces a blood glucose level database which associates the blood glucose level and the date/time of measurement of the measurement data and the sorted time slot with each other and stores the blood glucose level database, for example, into a folder corresponding to the patient name of the hard disk drive 14. Thereafter, the CPU 11 controls the display unit 15 to display such a graph display screen image 70 as shown in FIG. 8.

This graph display screen image 70 includes a menu bar 71 on which menu items which can be executed are displayed, a patient information field 72 in which patient information and so forth are displayed, a standby button 73 for establishing a standby mode, a logoff button 74 for logoff, a graph kind selection button display region 75 in which a plurality of buttons for selecting a type of a graph are displayed, a graph type selection button display region 76, and a graph display region 77 in which a graph is displayed.

In the patient information field 72, the name and a patient ID of a selected patient are displayed in a patient name display field 72A and a patient ID display field 72B, respectively, and a patient details button 72C, a new button 72D and a search button 72E are provided on the right side of the patient ID display field 72B.

The CPU 11 causes detailed information of the patient to be displayed if the patient details button 72C of the patient information field 72 is selected through the operation unit 16.

Further, the CPU 11 can register a new patient if the new button 72D of the patient information field 72 is selected through the operation unit 16.

Furthermore, if the search button 72E of the patient information field 72 is selected through the operation unit 16, then the CPU 11 causes the patient search screen image (FIG. 5) to be displayed so that a patient can be searched for again.

In the graph kind selection button display region 75, a trend button 75A, a period average button 75B, a 24 h trend button 75C, a rate button 75D, a My graph button 75E and a blood glucose level note button 75F are provided such that one of them is selected. By default, the trend button 75A is selected.

In the graph type selection button display region 76, a plurality of buttons for allowing selection of graph types individually corresponding to the trend button 75A, period average button 75B, 24 h trend button 75C, rate button 75D and My graph button 75E of the graph kind selection button display region 75 are displayed. If the trend button 75A is selected, then a whole time (all time) button 76A and a by-time slot button 76B are displayed. Incidentally, by default, the whole time button 76A is selected.

In the graph display region 77, graphs corresponding to a button selected by the graph kind selection button display region 75 (one of the trend button 75A, period average button 75B, 24 h trend button 75C, rate button 75D, My graph button 75E and blood glucose level note button 75F) and a button selected by the graph type selection button display region 76 (in this instance, the all time button 76A or the by-time slot button 76B) and various types of information relating to the graphs and so forth are displayed.

In this graph display region 77, when the trend button 75A and the all time button 76A are selected, a line graph 81 is displayed, and a period information display region 82, a blood glucose level information display region 83, a time slot selection check box 84, a legend display region 85, a comparison button 86 and a print button 87 are provided.

Here, in the time slot selection check box 84, "b.b." corresponds to "before breakfast"; "a.b." to "after breakfast"; "b.l." to "before lunch"; "a.l." to "after lunch"; "b.s." to "before supper"; "a.s" to "after supper"; "b.g." to "before going to bed"; and "l.n." to "late at night."

The CPU 11 causes the dates corresponding to the range of "one month" displayed in a range selection menu 82A in the period information display region 82 with reference to the date at present acquired from the clock unit 18 to be displayed in a start date display field 82B and an end date display field 82C. The range selection menu 82A is formed from a pull-down menu so that a range can be selected by the doctor and, for example, one of "one month," "two months," "three months" and "six months" can be selected. By default, "one month" is selectively displayed.

Together with this, the CPU 11 reads out the blood glucose level database corresponding to the patient name displayed in the patient name display field 72A from the hard disk drive 14 and extracts only the blood glucose levels of the time slots with regard to which a check is placed in the time slot selection check box 84 (in this instance, "before breakfast," "after breakfast," "after supper" and "late at night") within the range from the start date to the end date displayed in the start date display field 82B and the end date display field 82C based on the date/time of measurement, respectively, from the blood glucose level database.

Then, the CPU 11 plots the extracted blood glucose levels with a symbol for each time slot along the time series and then interconnects the mutually adjacent symbols with a straight line to produce the line graph 81. With the all time button 76A selected, the extracted blood glucose levels are interconnected by a single line.

Here in the line graph 81, the axis of abscissa indicates the date and the axis of ordinate indicates the blood glucose level (mg/dl). Further, the line graph 81 is divided into a plurality of regions (which may be visually distinguishable, such as for example by color) in response to the blood glucose level. For example, a region within which the blood glucose level is 0 to 59 [mg/dl] and is determined to be that of hypoglycemia is determined as a hypoglycemia region 81A, for example, of green; another region within which the blood glucose level is 60 to 109 [mg/dl] and is determined normal is determined as a normal region 81B, for example, of white; a further region within which the blood glucose level is 110 to 125 [mg/dl] and is determined intermediate between a normal level and a level of hyperglycemia is determined as a pseudopositive region 81C, for example, of yellow; and a still further region within which the blood glucose level is 126 to 400 [mg/dl] and is determined to be that of hyperglycemia is determined as a hyperglycemia region 81D, for example, of pink.

Further, in the line graph 81, a so-called gradation display form is used wherein the coloring in the proximity of a boundary of each of the hypoglycemia region 81A, normal region 81B, pseudopositive region 81C and hyperglycemia region 81D is gradually changed from one color to the other color.

Furthermore, in the line graph 81, in the case where a plotted blood glucose level is within 0 to 59 [mg/gl] or higher than 126 [mg/dl] as shown in the legend display region 85, the symbol of the plotted blood glucose level is displayed emphatically so that it can be visually confirmed readily by the doctor.

Further, the CPU 11 calculates an average value, a standard deviation value, a maximum value, a minimum value and the data number of the blood glucose levels extracted from the blood glucose level database and displays the average value, standard deviation value, maximum value, minimum value and data number in an average value display field 83A, a standard deviation value display field 83B, a maximum value display field 83C, a minimum value display field 83D and a measurement time number display field 83E of the blood glucose level information display region 83, respectively.

A slide bar 88 for moving a reference (in this instance, reference day) is provided at a lower portion of the line graph 81.

Figure 9:
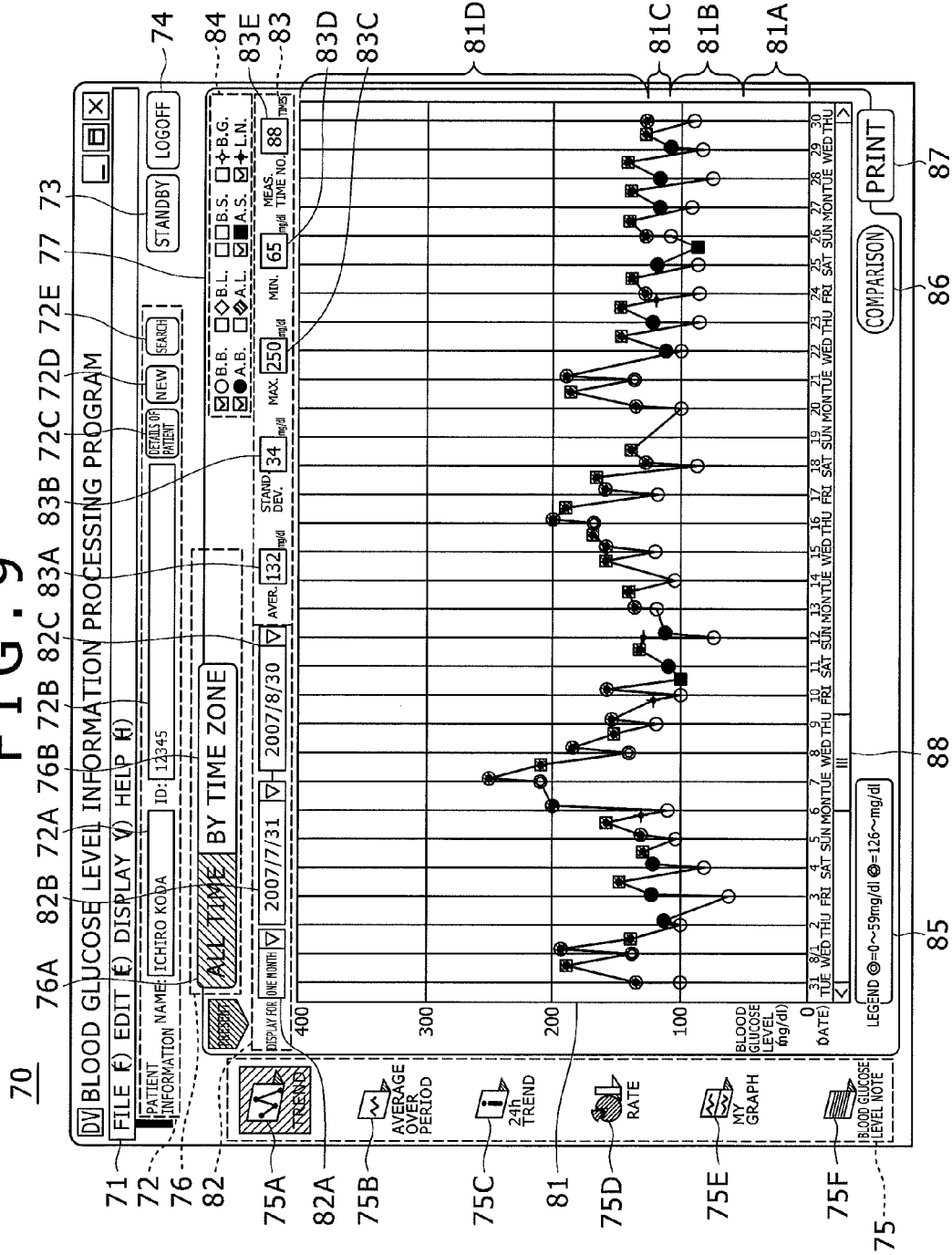
FIG. 9 is a schematic illustration of another configuration of the graph display screen image displaying a line graph over the whole time.

As shown in FIG. 9, if the slide bar 88 is operated to move through the operation unit 16, then the CPU 11 backdates the reference day in response to the amount of movement of the slide bar 88, and extracts only the blood glucose levels for one month till the backdated reference date from the blood glucose level database again. Then, the CPU 11 re-plots the blood glucose levels on the line graph 81 with symbols for the individual time slots along the time series.

At this time, the CPU 11 causes the backdated reference day to be displayed in the end date display field 82C and causes the start date display field 82B to display the date prior by one month to the reference day. Further, the CPU 11 calculates the average value, standard deviation value, maximum value, minimum value and data number of the blood glucose levels re-extracted from the blood glucose level database again. Then, the CPU 11 causes the average value, standard deviation value, maximum value, minimum value and data number to be displayed in the average value display field 83A, standard deviation value display field 83B, maximum value display field 83C, minimum value display field 83D and measurement time number display field 83E of the blood glucose level information display region 83, respectively.

In this manner, if the slide bar 88 is operated to move, then the blood glucose level information processing apparatus 2 can change only the dates while the range within which blood glucose levels are to be plotted on the line graph 81 is kept fixed.

If, for example, the "three months" in the range selection menu 82A of the period information display region 82 is selected through the operation unit 16, then the CPU 11 changes the axis of abscissa of the line graph 81 from that for one month to that for three months and plots blood glucose levels within three months on the line graph 81 with symbols for individual time slots along the time series.

Figure 10:
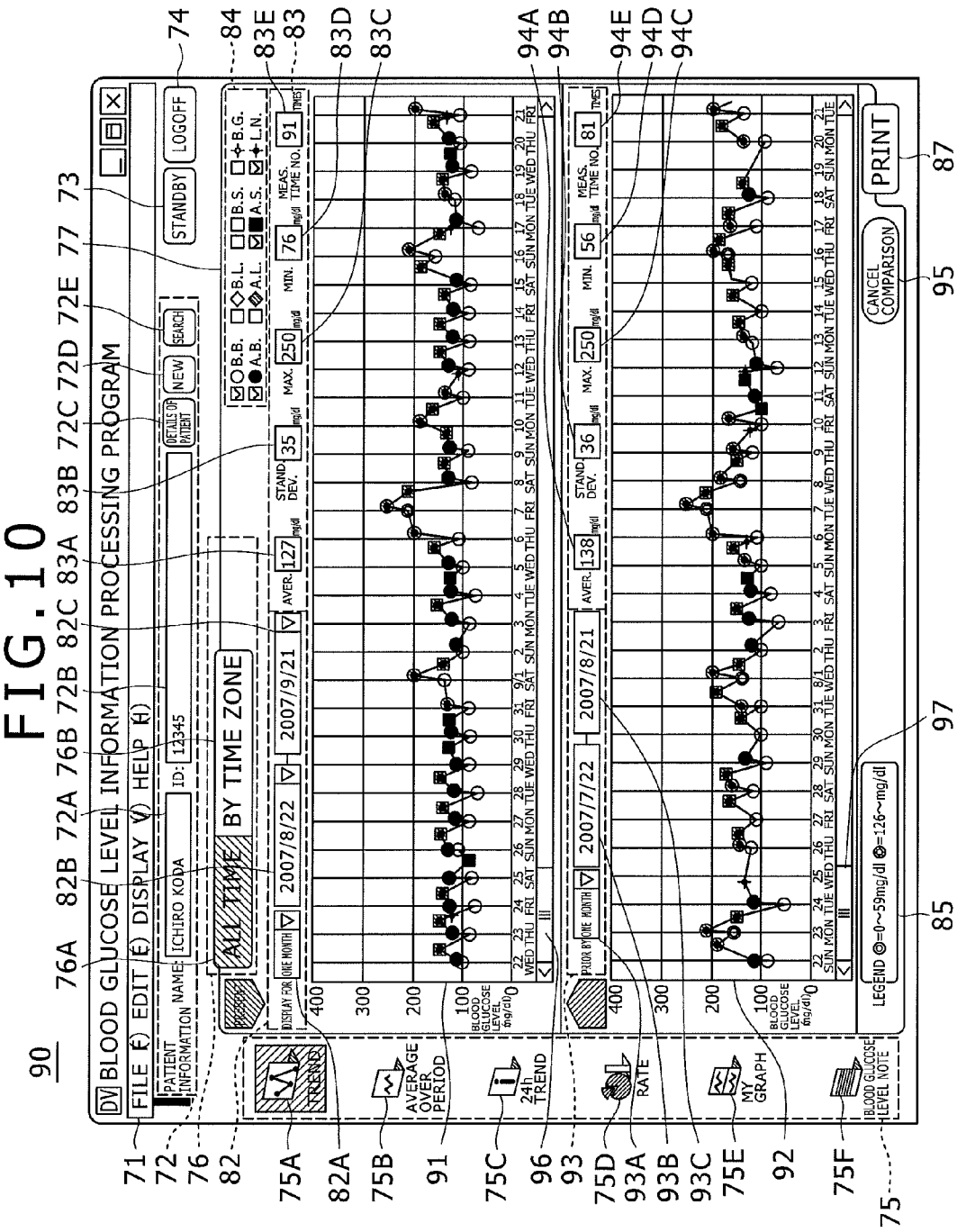
FIG. 10 is a schematic illustration of a configuration of a graph display screen image in which a line graph over the whole time in the case where a comparison button is selected is displayed.

If the comparison button 86 of the graph display screen image 70 is selected through the operation unit 16, then the CPU 11 displays, in the graph display region 77 on the display unit 15, a graph display screen image 90 on which a line graph 91 obtained by reducing the period information display region 82, blood glucose level information display region 83, time slot selection check box 84, legend display region 85 and line graph 81 in the vertical direction; another line graph 92; a comparison period information display region 93; a comparison blood glucose information display region 94; a comparison cancellation button 95; and a print button 87, respectively, as shown in FIG. 10 in which corresponding elements to those in FIG. 8 are denoted by like reference symbols.

In particular, the CPU 11 displays "one month" same as that in the range selection menu 82A in a period selection menu 93A of the comparison period information display region 93, and causes a comparison start date and a comparison end date, which correspond to the range of "one month" immediately preceding to the start date displayed in the start date display field 82B, to be displayed in a comparison start date display field 93B and a comparison end date display field 93C, respectively.

Further, the CPU 11 extracts blood glucose levels dated from the comparison start date to the comparison end date displayed in the comparison start date display field 93B and the comparison end date display field 93C based on the measurement date/time from the blood glucose level database read out from the hard disk drive 14. Then, the CPU 11 plots only the blood glucose levels within the time slots with regard to which a check is placed in the time slot selection check box 84 (in this instance, "before breakfast," "after breakfast," "after supper" and "late at night") with symbols for the individual time slots along the time series. Then, the CPU 11 connects each mutually adjacent symbols to each other with a straight line to produce the line graph 92.

Then, the CPU 11 causes the line graph 91 and the line graph 92 to be displayed in an upwardly and downwardly juxtaposed relationship with each other in the graph display region 77.

Further, the CPU 11 calculates the average value, standard deviation value, maximum value, minimum value and data number of the blood glucose levels plotted on the line graph 92. Then, the CPU 11 causes the average value, standard deviation value, maximum value, minimum value and data number to be displayed in the average value display field 94A, standard deviation value display field 94B, maximum value display field 94C, minimum value display field 94D and measurement time number display field 94E of the comparison blood glucose level information display region 94, respectively.

Further, if a slide bar 96 provided at a lower portion of the line graph 91 is operated to move through the operation unit 16, then the CPU 11 backdates the reference day in response to the amount of movement of the slide bar 96. Then, the CPU 11 re-plots only the blood glucose levels for one month till the backdated reference day on the line graph 91 with symbols for the individual time slots along the time series. Further, also with regard to the line graph 92, the CPU 11 re-plots the blood glucose levels backdating by a number of days equal to that of the line graph 91.

When a slide bar 97 provided at a lower portion of the line graph 92 is operated to move through the operation unit 16, the CPU 11 backdates the reference day in response to the amount of movement of the slide bar 97. Then, the CPU 11 re-plots only the blood glucose levels for one month till the backdated reference day on the line graph 92 with symbols for the individual time slots along the time series. Also with regard to the line graph 91, the CPU 11 re-plots the blood glucose levels backdating by a number of days equal to that of the line graph 92.

Further, if the comparison cancellation button 95 of the graph display screen image 90 is selectively operated through the operation unit 16, then the CPU 11 controls the display unit 15 to display the graph display screen image 70 (FIG. 8) again.

Figure 11:
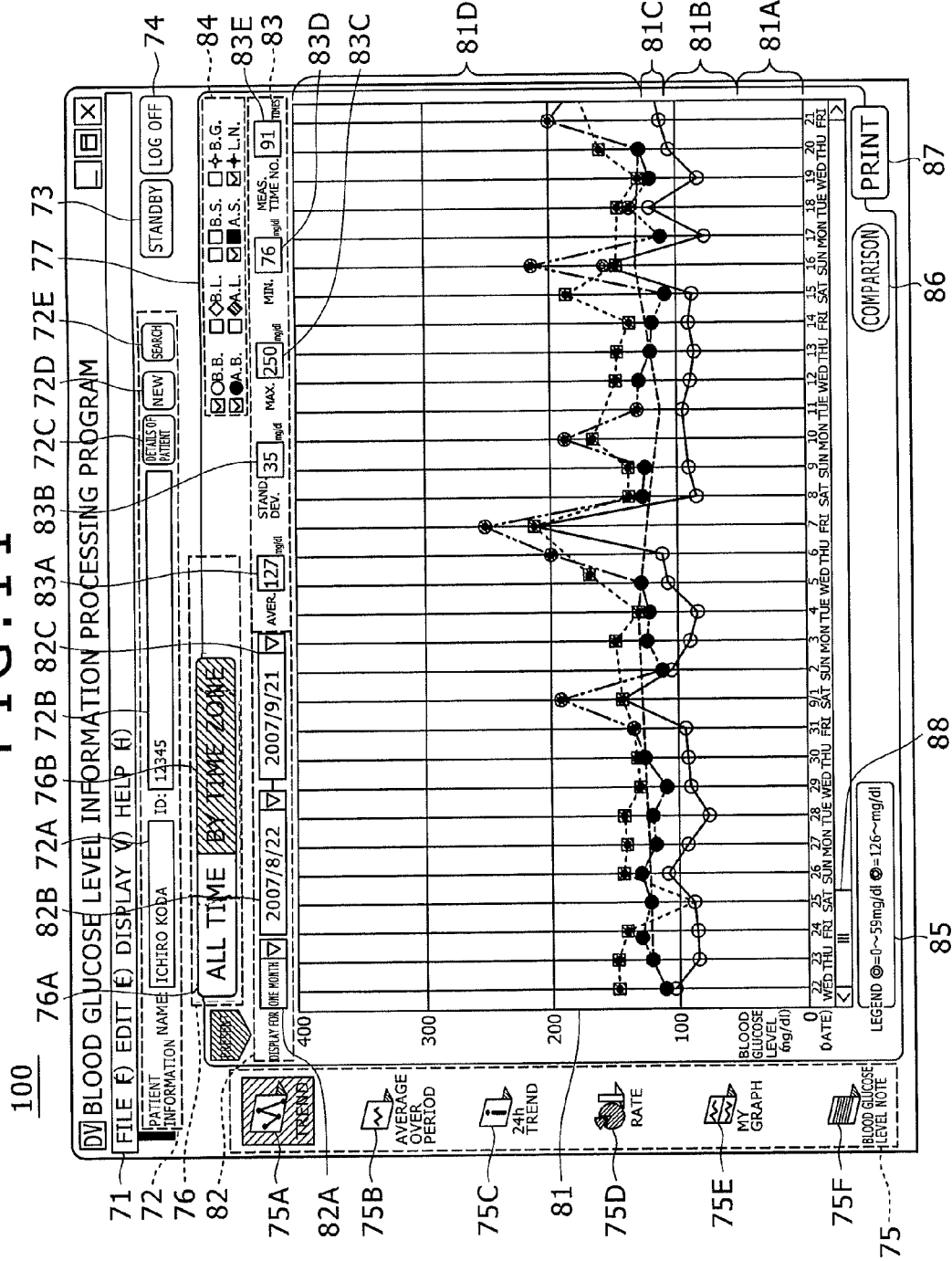
FIG. 11 is a schematic illustration of a configuration of a graph display screen image in which a by-time slot line graph is displayed.

If, for example, the by-time slot (by-time zone) button 76B of the graph type selection button display region 76 of the graph display screen image 70 (FIG. 8) is selectively operated through the operation unit 16, the CPU 11 controls the display unit 15 to display a graph display screen image 100 in which a line graph 101 is displayed in the graph display region 77 as illustrated in FIG. 11 in which like elements to those in FIG. 8 are denoted by like reference symbols. When the by-time zone button 76B is selected, the data associated with the time zones checked in the time slot selection check box 84 is displayed, with the respective lines interconnecting the data of the respective time slots (e.g., one line interconnecting the before breakfast data, one line interconnecting the after breakfast data, etc.).

At this time, the CPU 11 extracts the blood glucose levels dated from the start date to the end date displayed in the start date display field 82B and the period information display region 82, respectively, based on the date/time of measurement from the blood glucose level database read out from the hard disk drive 14. Then, the CPU 11 plots only those blood glucose levels within the time slots with regard to which a check is placed in the time slot selection check box 84 (in this instance, "before breakfast," "after breakfast," "after supper" and "late at night") such that they are connected to each other with a straight line for each of the symbols in the time slots to produce the graph display screen image 100.

Further, if the slide bar 88 provided at a lower portion of the line graph 101 is operated to move through the operation unit 16 by the doctor, then the CPU 11 backdates the reference day in response to the amount of movement of the slide bar 88 and re-plots only the blood glucose levels within one month till the backdated reference day on the line graph 101 such that they are connected to each other with straight lines for the individual symbols in the time slots.

Furthermore, if the comparison button 86 of the graph display screen image 100 is selectively operated through the operation unit 16, then the CPU 11 displays the line graph 101 in a reduced scale in the vertical direction on the upper side of the graph display region 77 and causes a line graph within the same range as that of the line graph 101 but within the immediately preceding period to be displayed on the lower side of the graph display region 77 in a manner similar to the case where the graph display screen image 90 is displayed when the comparison button 86 of the graph display screen image 70 described hereinabove is selectively operated.

Figure 12:
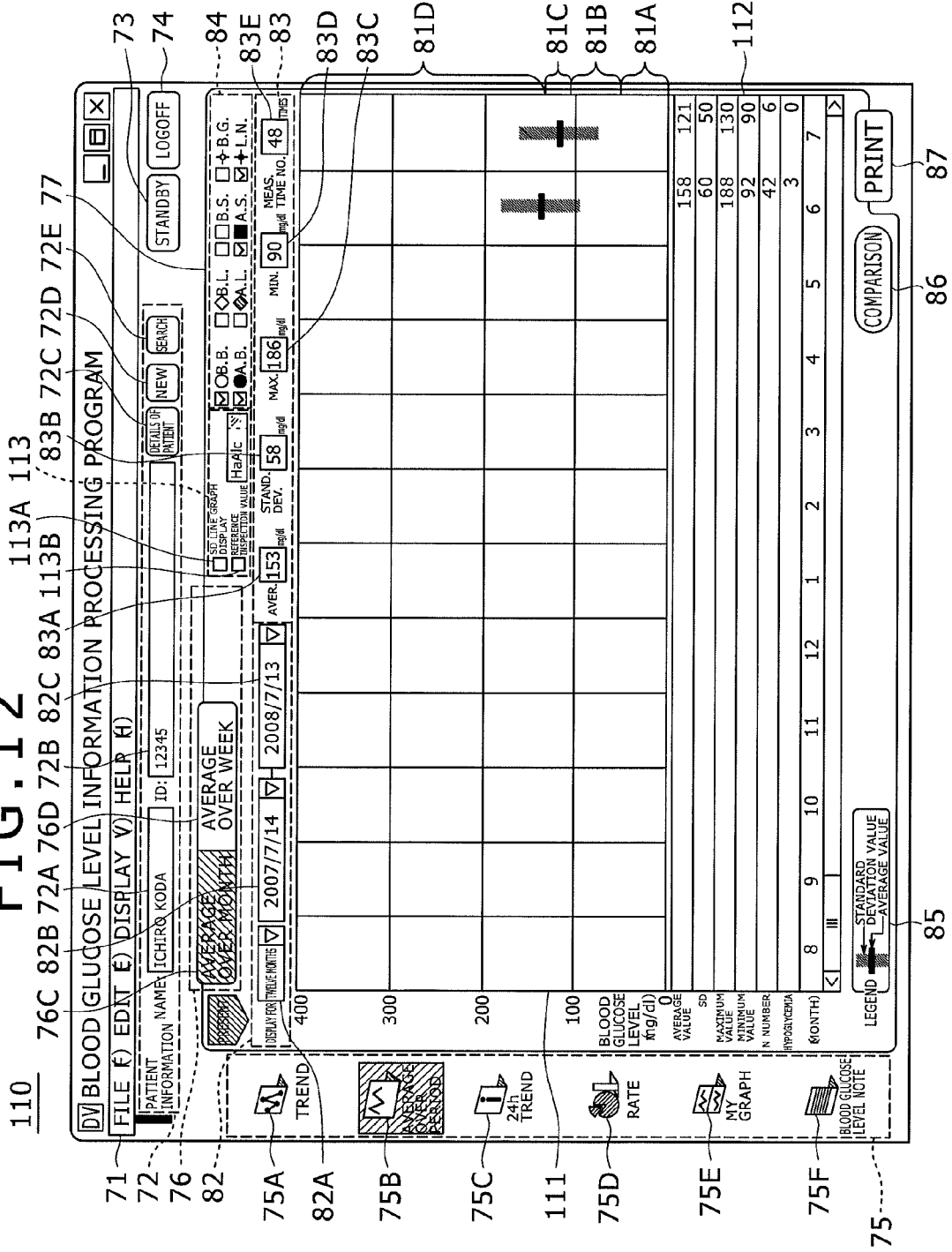
FIG. 12 is a schematic illustration of a configuration of a graph display screen image in which an average graph of monthly averages is displayed.

If, for example, the average over period button 75B of the graph kind selection button display region 75 in the graph display screen image 70 (FIG. 8) is selectively operated through the operation unit 16, the CPU 11 controls the display unit 15 to display a graph display screen image 110 as illustrated in FIG. 12 in which corresponding elements to those in FIG. 8 are denoted by like reference symbols.

In this graph display screen image 110, a average over month button 76C and an average over week button 76D are displayed in the graph type selection button display region 76, and a period information display region 82, a blood glucose level information display region 83, a time slot selection check box 84, a legend display region 85, an average graph 111, a blood glucose level information table 112 and an additional check box field 113 are provided in the graph display region 77. In this instance, the range selection menu 82A allows selection of, for example, "12 months," "24 months" and "36 months," and by default, "12 months" is selectively displayed.

When the graph display screen image 110 is to be displayed on the display unit 15, the CPU 11 extracts the blood glucose levels within the time slots with regard to which a check is placed in the time slot selection check box 84 (in this instance, "before breakfast," "after breakfast," "after supper" and "late at night") within the period displayed in the start date display field 82B and the end date display field 82C from the blood glucose level database for each month based on the date and hour of measurement.

Then, the CPU 11 calculates an average value, a standard deviation value, a maximum value, a minimum value and a data number of the blood glucose levels extracted for each month and the number of times of hypoglycemia (0 to 59 [mg/dl]).

Further, the CPU 11 causes the average graph 111, which indicates the calculated average value and standard deviation value for 12 months as a horizontal line and a vertical bar, respectively, to be displayed in the graph display region 77 and causes the average value, standard deviation value (SD), maximum value, minimum value and data number (N number) of the blood glucose levels and the number of times of hypoglycemia calculated for each month to be displayed in the blood glucose level information table 112.

If the comparison button 86 of the graph display screen image 110 is selectively operated through the operation unit 16, then the CPU 11 causes the average graph 111 to be displayed in a reduced scale in the vertical direction on the upper side of the graph display region 77 and causes an average graph within the same range as that of the average graph 111 within an immediately preceding period in a manner similar to the case where the graph display screen image 90 is displayed when the comparison button 86 of the graph display screen image 70 described hereinabove is selectively operated.

Figure 13:
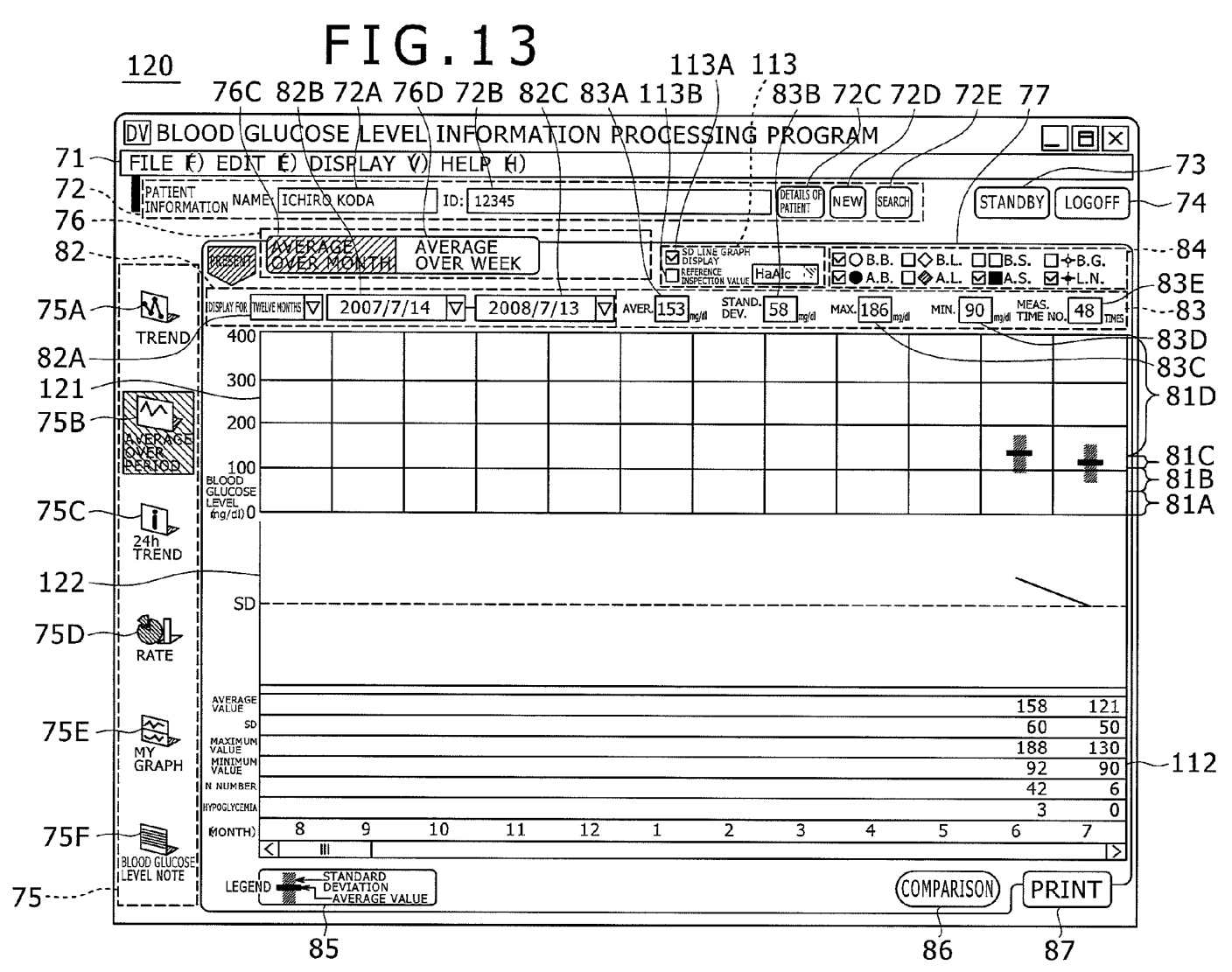

If an SD line display check box A of the additional check box field 113 in the graph display screen image 110 is selectively operated through the operation unit 16, the CPU 11 causes a graph display screen image 120, in which a standard deviation line graph 122 wherein standard deviation values for individual months are connected by straight lines is displayed, to be displayed between an average graph 121 obtained by reducing the average graph 111 in the vertical direction and the blood glucose level information table 112. This is generally shown in FIG. 13.

Further, if a reference inspection value check box 113B of the additional check box field 113 in the graph display screen image 110 is selectively operated through the operation unit 16, then the CPU 11 can display, for example, HbA1c values and so forth for individual months registered in the patient database or the like as a line graph.

If the comparison button 86 of the graph display screen image 120 is selectively operated through the operation unit 16, then the CPU 11 causes the average graph 111 and the standard deviation line graph 122 to be displayed in a reduced scale in the vertical direction on the upper side of the graph display region 77 and causes an average graph and a standard deviation line graph within the same range as that of the average graph 111 and the blood glucose level information table 112 within an immediately preceding period to be displayed on the lower side of the graph display region 77 in a manner similar to the case where the graph display screen image 90 is displayed when the comparison button 86 of the graph display screen image 70 described above is selectively operated.

Figure 14:
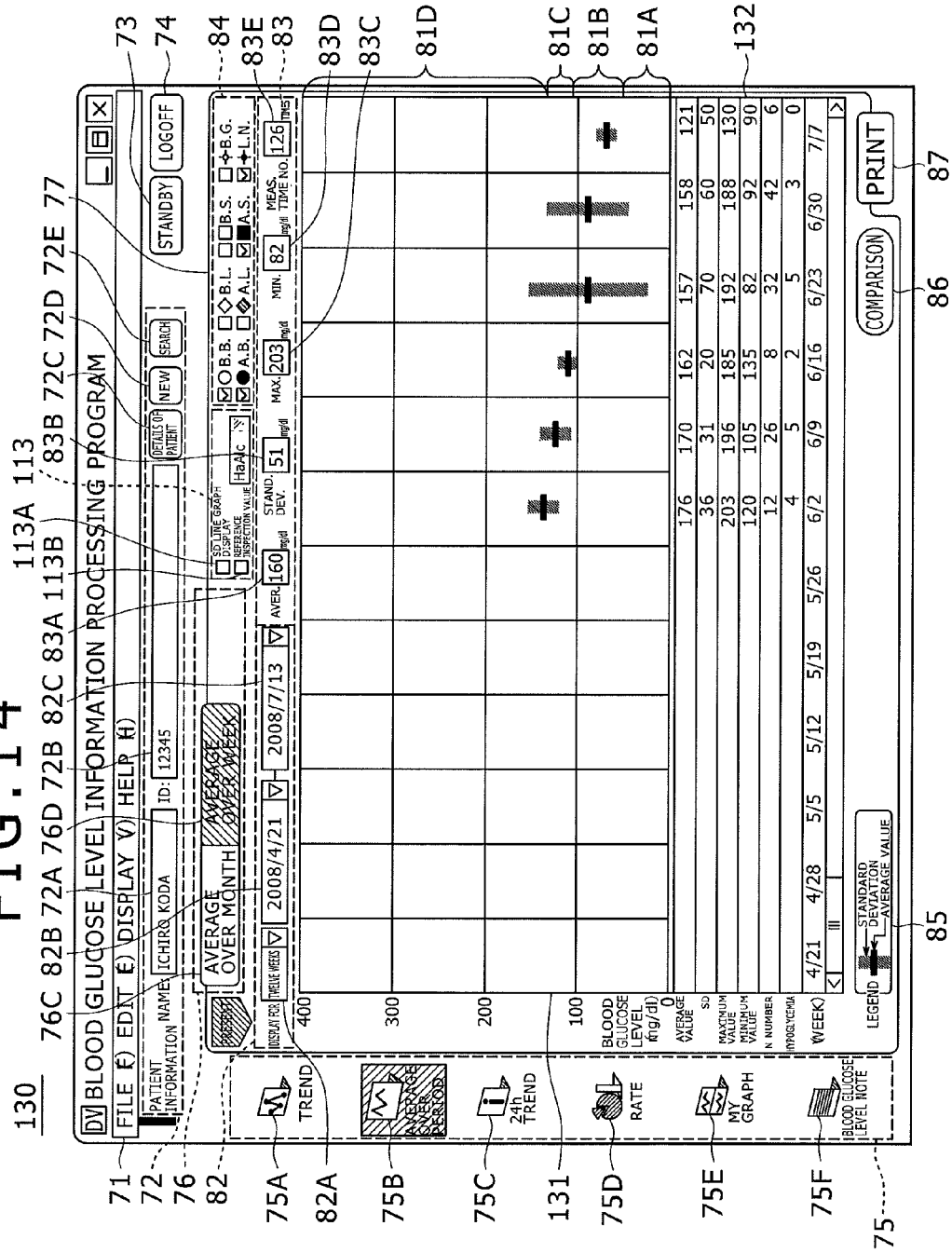
FIG. 14 is a schematic illustration of a configuration of a graph display screen image in which an average graph of weekly averages is displayed.

On the other hand, if the average over week button 76D of the graph type selection button display region 76 in the graph display screen image 110 (FIG. 12) is selectively operated through the operation unit 16, then the CPU 11 controls the display unit 15 to display such a graph display screen image 130 as shown in FIG. 14 in which corresponding elements to those in FIG. 12 are denoted by like reference symbols.

In this instance, in the graph display screen image 130, the range selection menu 82A can allow selection of, for example, "12 weeks," "24 weeks" and "36 weeks," and by default, "12 weeks" is selectively displayed.

When the graph display screen image 130 is displayed on the display unit 15, the CPU 11 extracts blood glucose levels within the time slots with regard to which a check is placed in the time slot selection check box 84 (in this instance, "before breakfast," "after breakfast," "after supper" and "late at night") within the period displayed in the start date display field 82B and the end date display field 82C from the blood glucose level database for each week based on the date/time of measurement.

Then, the CPU 11 calculates an average value, a standard deviation value, a maximum value, a minimum value and a data number of the blood glucose levels extracted for each week and the number of times of hypoglycemia (0 to 59 [mg/dl]).

Further, the CPU 11 causes an average graph 131, which indicates the calculated average value and standard deviation value for 12 weeks as a horizontal line and a vertical bar, respectively, to be displayed in the graph display region 77. Further, the CPU 11 causes the calculated average value, standard deviation value, maximum value, minimum value and data number of the blood glucose levels and the number of times of hypoglycemia for each week to be displayed in a blood glucose level information table 132.

If the comparison button 86 of the graph display screen image 130 is selectively operated through the operation unit 16, then the CPU 11 causes the average graph 131 to be displayed in a reduced scale in the vertical direction on the upper side of the graph display region 77 and causes the average graph within the same range as that of the average graph 131 but within an immediately preceding period to be displayed on the lower side of the graph display region 77 similarly as in the case where the graph display screen image 90 is displayed when the comparison button 86 of the graph display screen image 70 described hereinabove is selectively operated.

Figure 15:
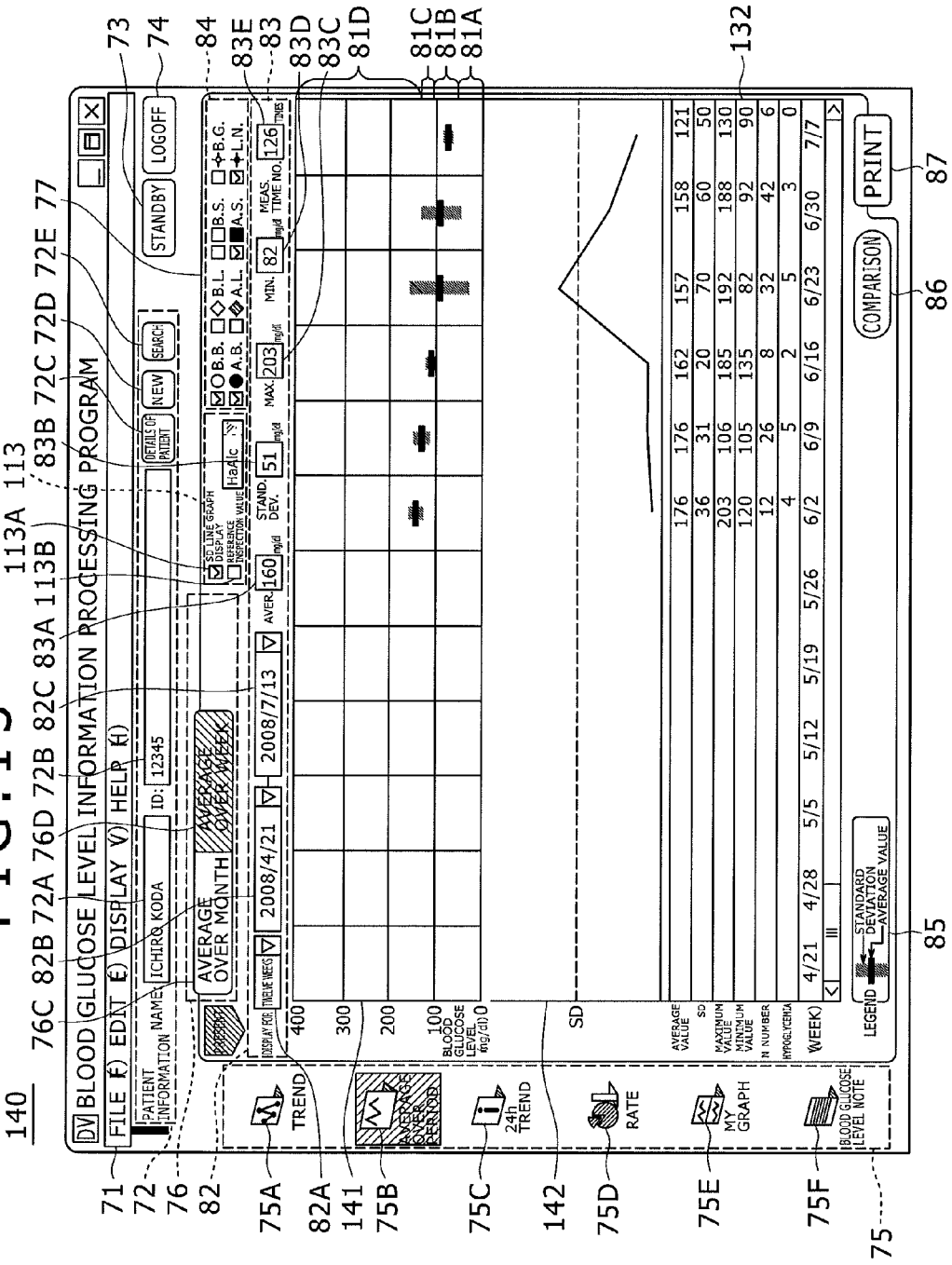
FIG. 15 is a schematic illustration of a configuration of a graph display screen image in which an average graph and a standard deviation line graph of weekly averages are displayed.

If an SD line display check box 113A of the additional check box field 113 in the graph display screen image 130 is selectively operated through the operation unit 16, then the CPU 11 causes a graph display screen image 140, in which a standard deviation line graph 142 wherein standard deviation values for individual weeks are connected by straight lines is displayed, to be displayed between an average graph 141 obtained by reducing the average graph 131 in the vertical direction and the blood glucose level information table 132 as illustrated in FIG. 15 in which corresponding elements to those in FIG. 14 are denoted by like reference symbols.

If the comparison button 86 of the graph display screen image 140 is selectively operated through the operation unit 16, then the CPU 11 causes the average graph 141 and the standard deviation line graph 142 to be displayed in a reduced scale in the vertical direction on the upper side of the graph display region 77 and causes an average graph and a standard deviation line graph within the range same as that of the average graph 141 and the standard deviation line graph 142 but within an immediately preceding period to be displayed on the lower side of the graph display region 77 in a manner similar to the case where the graph display screen image 90 is displayed when the comparison button 86 of the graph display screen image 70 described hereinabove is selectively operated.

Figure 16:
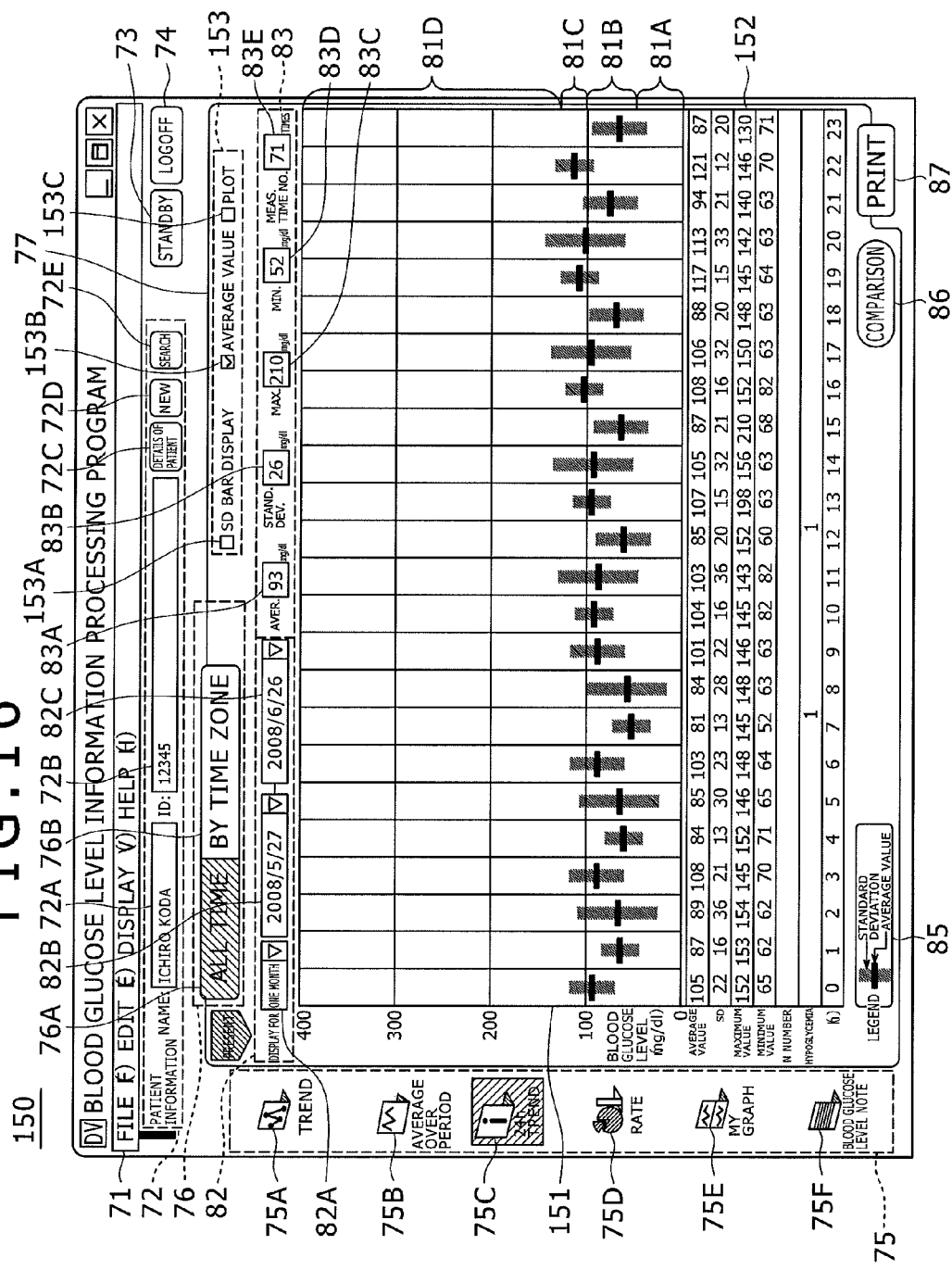
FIG. 16 is a schematic illustration of a configuration of a graph display screen image in which an average graph for each one hour is displayed.

If, for example, the 24 h (24 hour) trend button 75C of the graph kind selection button display region 75 in the graph display screen image 70 (FIG. 8) is selectively operated through the operation unit 16, then the CPU 11 controls the display unit 15 to display a graph display screen image 150 as illustrated in FIG. 16 in which corresponding elements to those in FIG. 8 are denoted by like reference symbols.

In this graph display screen image 150, an all time button 76A and a by time zone (by time slot) slot button 76B are displayed in the graph type selection button display region 76. A period information display region 82, a blood glucose information display region 83, a legend display region 85, a comparison button 86, a print button 87, an average graph 151, a blood glucose level information table 152 and a check box field 153 are provided in the graph display region 77.

In this graph display screen image 150, the range selection menu 82A is configured to allow selection of, for example, "one month," "two months," "three months" and "six months," and by default, "one month" is selectively displayed.

In the check box field 153, an SD bar display check box 153A, an average value check box 153B and a plot check box 153C are provided, and by default, a check is placed in the average value check box 153B.

When the graph display screen image 150 is displayed on the display unit 15, the CPU 11 extracts blood glucose levels within a period displayed in the start date display field 82B and the end date display field 82C from the blood glucose level database for each one hour based on the date/time of measurement. Then, the CPU 11 calculates the average value, standard deviation value, maximum value, minimum value, data number and number of times of hypoglycemia of the blood glucose levels extracted for each one hour.

Then, the CPU 11 causes the average graph 151, which indicates the average value and the standard deviation value calculated for each one hour as a horizontal line and a vertical bar, respectively, to be displayed in the graph display region 77. Then, the CPU 11 causes the average value, standard deviation value, maximum value, minimum value, data number and number of hypoglycemia for each one hour to be displayed in the blood glucose level information table 152.

If the comparison button 86 of the graph display screen image 150 is selectively operated through the operation unit 16, then the CPU 11 causes the average graph 151 to be displayed in a reduced scale in the vertical direction on the upper side of the graph display region 77 and causes the average graph within the same range as that of the average graph 151 but within an immediately preceding period to be displayed on the lower side of the graph display region 77 similarly as in the case where the graph display screen image 90 is displayed when the comparison button 86 of the graph display screen image 70 described hereinabove is selectively operated.

Figure 17:
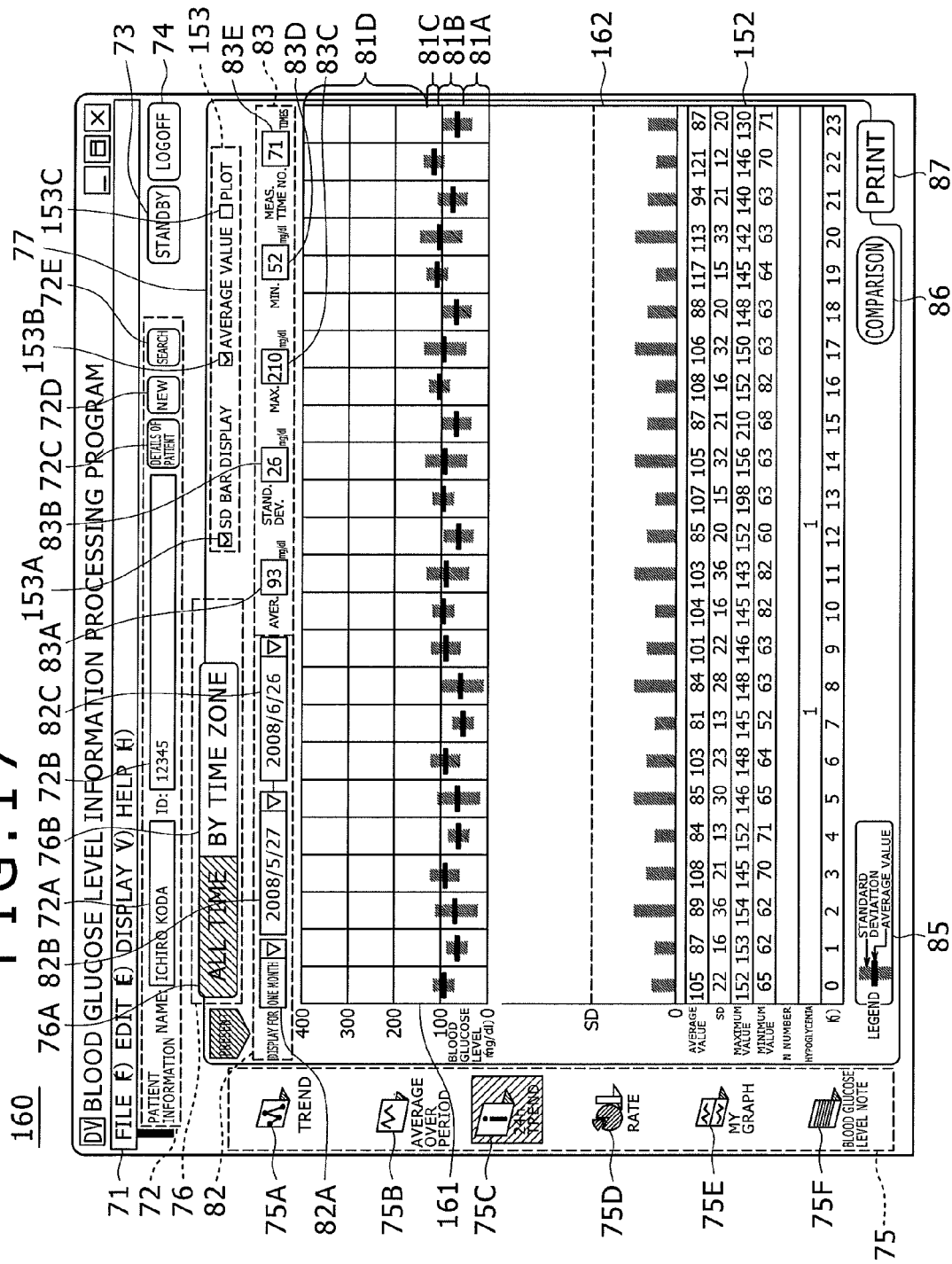
FIG. 17 is a schematic illustration of a configuration of a graph display screen image in which an average graph and a standard deviation line graph for each one hour are displayed.

If an SD line display check box 153A of the check box field 153 in the graph display screen image 150 is selectively operated through the operation unit 16, then the CPU 11 causes a graph display screen image 160 shown in FIG. 17, in which a bar graph 162 wherein standard deviation values for each one hour represented by bars is displayed, to be displayed between an average graph 161 obtained by reducing the average graph 151 in the vertical direction and the blood glucose level information table 152.

If the comparison button 86 of the graph display screen image 160 is selectively operated through the operation unit 16, then the CPU 11 causes the average graph 161 and the bar graph 162 to be displayed in a reduced scale in the vertical direction on the upper side of the graph display region 77 and causes an average graph and a bar graph within the range same as that of the average graph 161 and the bar graph 162 but within an immediately preceding period to be displayed on the lower side of the graph display region 77 in a manner similar to the case where the graph display screen image 90 is displayed when the comparison button 86 of the graph display screen image 70 described hereinabove is selectively operated.

Figure 18:
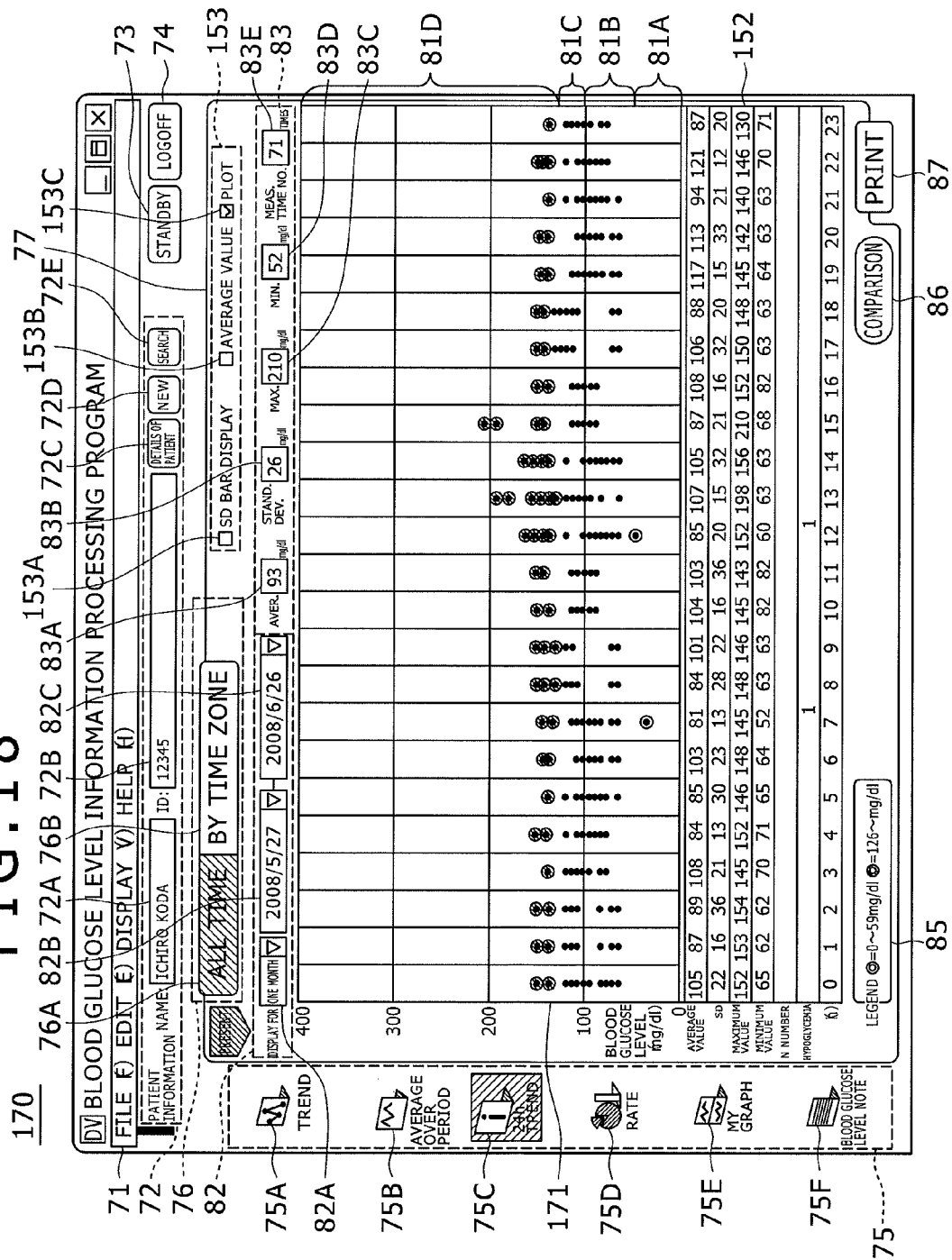
FIG. 18 is a schematic illustration of a configuration of a graph display screen image in which a plot graph for each one hour is displayed.

If the plot check box 153C of the check box field 153 in the graph display screen image 150 (FIG. 16) is selectively operated through the operation unit 16, then the CPU 11 causes such a graph display screen image 170 as illustrated in FIG. 18 in which corresponding elements to those in FIG. 16 are denoted by like reference symbols to be displayed. At this time, the CPU 11 places a check into the plot check box 153C of the check box field 153 and removes the check of the average value check box 153B. It is to be noted that, while the blood glucose levels used in FIGS. 16 and 18 are actually the same as each other, for the convenience of description, different blood glucose levels are used in FIGS. 16 and 18 and the values of the average graph 151 of FIG. 16, a plot graph 171 of FIG. 18 and the blood glucose level information table 152 are merely an example of such blood glucose levels.

Further, the CPU 11 causes a plot graph 171, wherein all extracted blood glucose levels for one month are sorted for each one hour and plotted, to be displayed in the graph display region 77 of the graph display screen image 170.

With the plot graph 171, in the case where the plotted blood glucose levels range from 0 to 59 [mg/dl] or are higher than 126 [mg/dl] as indicated in the legend display region 85, if the plot points of the plotted blood glucose levels are displayed emphatically, then they can be visually confirmed readily by the doctor.

If the comparison button 86 of the graph display screen image 170 is selectively operated through the operation unit 16, then the CPU 11 causes the plot graph 171 to be displayed in a reduced scale in the vertical direction on the upper side of the graph display region 77 and causes a plot graph within the range same as that of the plot graph 171 but within an immediately preceding period to be displayed on the lower side of the graph display region 77 in a manner similar to the case where the graph display screen image 90 is displayed when the comparison button 86 of the graph display screen image 70 described hereinabove is selectively operated.

Figure 19:
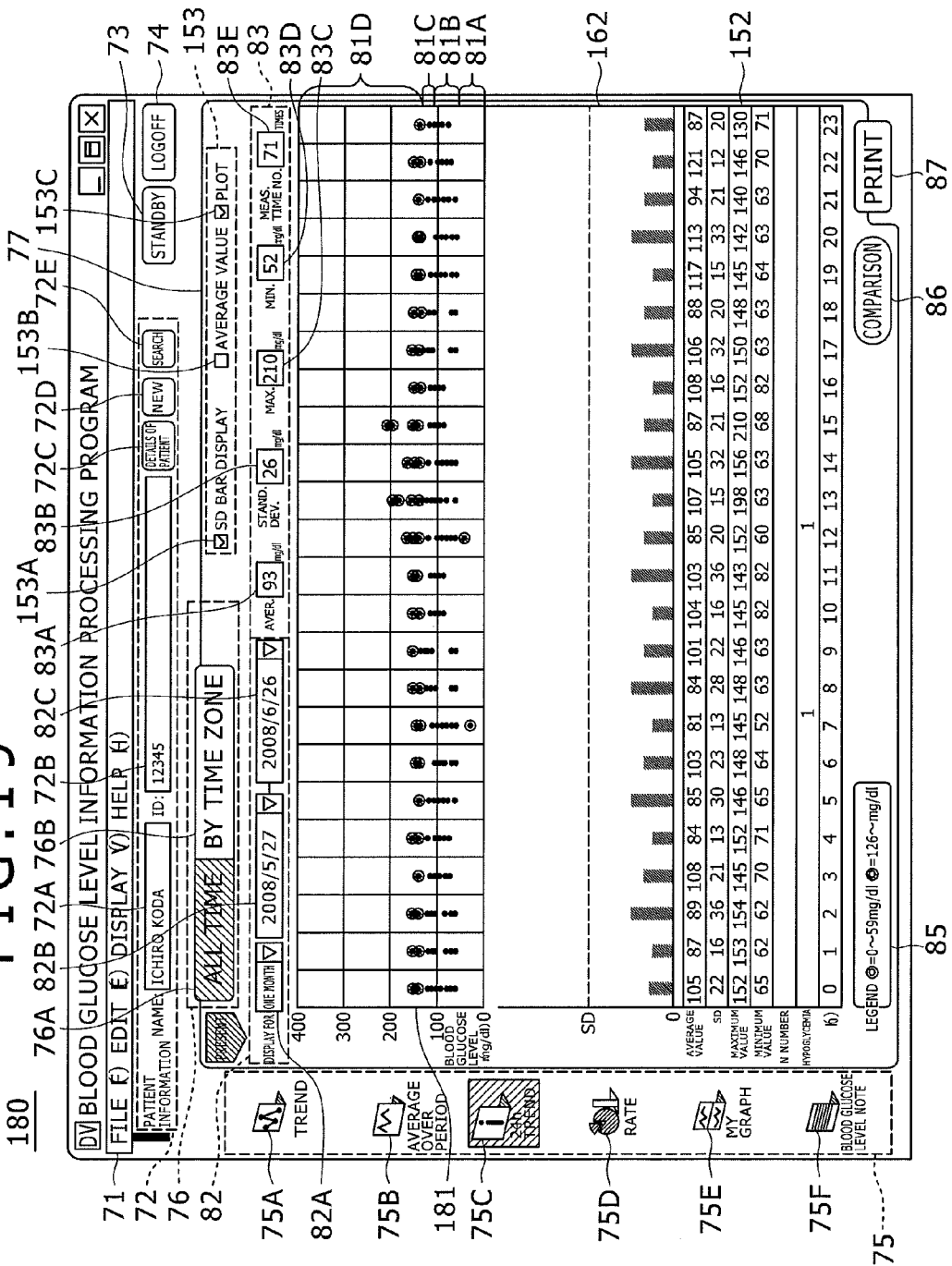
FIG. 19 is a schematic illustration of a configuration of a graph display screen image in which a plot graph and a standard deviation line graph for each one hour are displayed.

On the other hand, if an SD bar display check box 153A of the check box field 153 in the graph display screen image 170 is selectively operated through the operation unit 16, then the CPU 11 causes a graph display screen image 180, in which a bar graph 162 wherein standard deviation values for each one hour indicated as bars is displayed, to be displayed between a plot graph 181 obtained by reducing the plot graph 171 in the vertical direction and the blood glucose level information table 152 as illustrated in FIG. 19 in which corresponding elements to those in FIGS. 17 and 18 are denoted by like reference symbols.

If the comparison button 86 of the graph display screen image 180 is selectively operated through the operation unit 16, then the CPU 11 causes the plot graph 181 and the bar graph 162 to be displayed in a reduced scale in the vertical direction to be displayed on the upper side of the graph display region 77 and causes a plot graph and a bar graph within the range same as that of the plot graph 181 and the bar graph 162 but within an immediately preceding period to be displayed on the lower side of the graph display region 77 in a manner similar to the case where the graph display screen image 90 is displayed when the comparison button 86 of the graph display screen image 70 described hereinabove is selectively operated.

Figure 20:
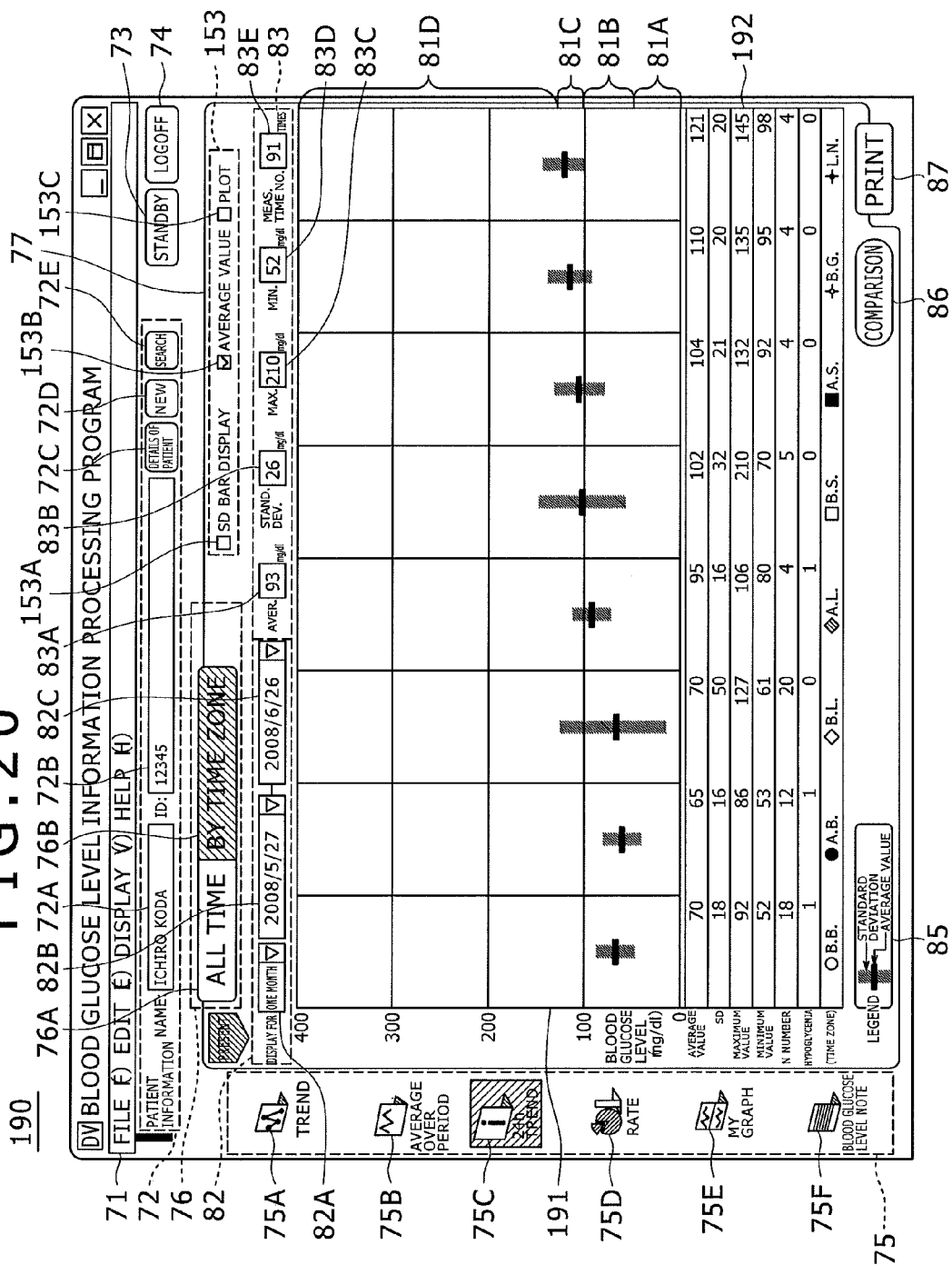
FIG. 20 is a schematic illustration of a configuration of a graph display screen image in which an average graph for each time slot is displayed.

If, for example, the by-time slot button 76B of the graph type selection button display region 76 in the graph display screen 150 (FIG. 16) is selectively operated through the operation unit 16, then the CPU 11 controls the display unit 15 to display a graph display screen image 190 as illustrated in FIG. 20 in which corresponding elements to those in FIG. 16 are denoted by like reference symbols.

When the graph display screen image 190 is to be displayed on the display unit 15, the CPU 11 extracts blood glucose levels within a period indicated in the start date display field 82B and the end date display field 82C corresponding to "one month" displayed by default in the range selection menu 82A from the blood glucose level database for each time slot based on the date/time of measurement.

Then, the CPU 11 calculates an average value, a standard deviation value, a maximum value, a minimum value and a data number of the blood glucose levels extracted for each time slot and the number of times of hypoglycemia.

Further, the CPU 11 causes an average graph 191, which indicates the calculated average value and standard deviation value for each time slot as a horizontal line and a vertical bar, respectively, to be displayed in the graph display region 77. Further, the CPU 11 causes the calculated average value, standard deviation value, maximum value, minimum value and data number of the blood glucose levels and the number of times of hypoglycemia for each time slot to be displayed in a blood glucose level information table 192.

If the comparison button 86 of the graph display screen image 190 is selectively operated through the operation unit 16, then the CPU 11 causes the average graph 191 to be displayed in a reduced scale in the vertical direction on the upper side of the graph display region 77 and causes an average graph within the same range as that of the average graph 191 but within an immediately preceding period to be displayed on the lower side of the graph display region 77 in a manner similar to the case where the graph display screen image 90 is displayed when the comparison button 86 of the graph display screen image 70 described hereinabove is selectively operated.

Figure 21:
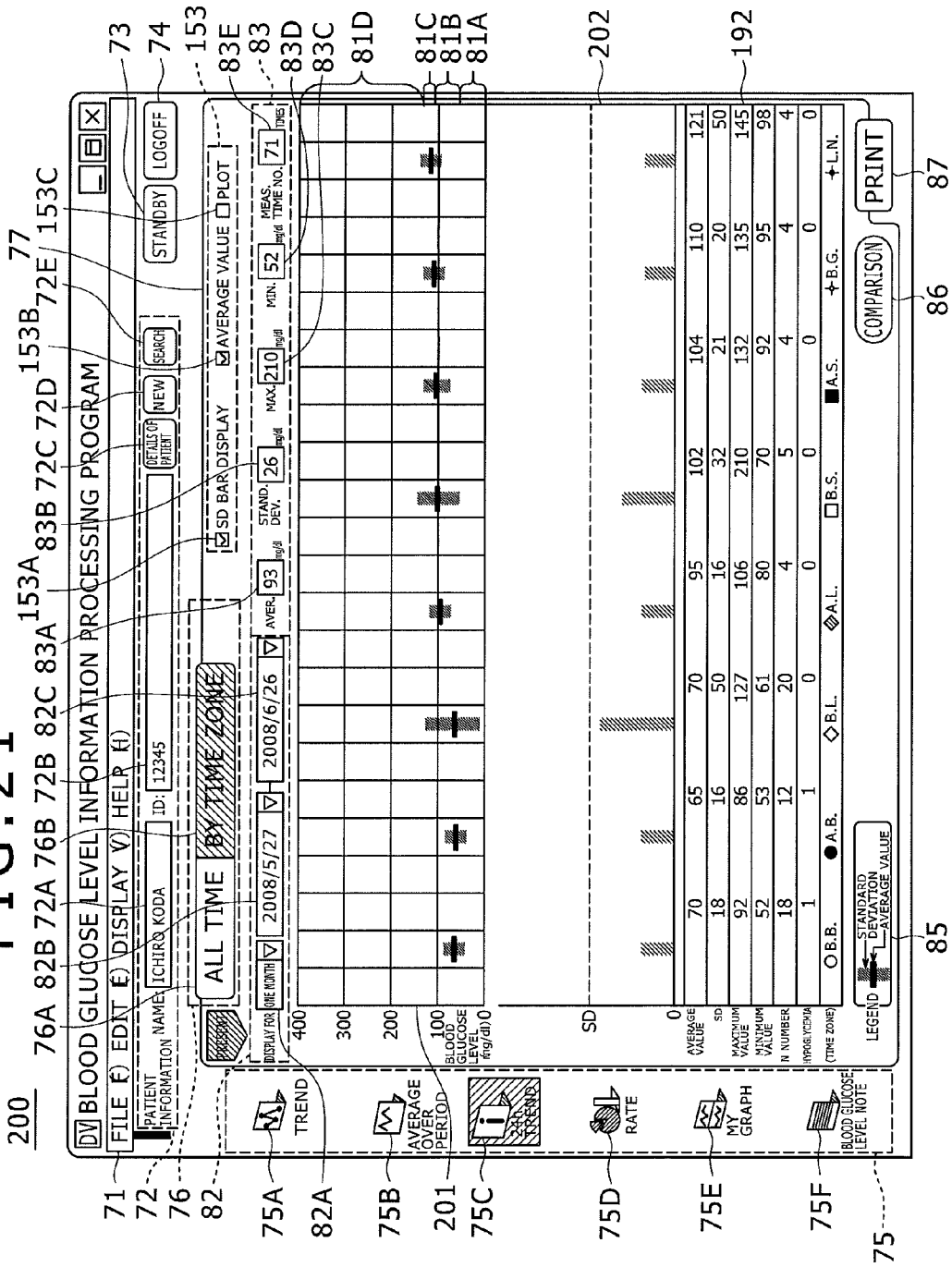
FIG. 21 is a schematic illustration of a configuration of a graph display screen image in which an average graph and a standard deviation line graph for each time slot are displayed.

If the SD bar display check box 153A of the check box field 153 in the graph display screen image 190 is selectively operated through the operation unit 16, then the CPU 11 causes a graph display screen image 200, in which a bar graph 202 wherein standard deviation values for each time slot are indicated as bars is displayed between an average graph 201 obtained by reducing the average graph 191 in the vertical direction and the blood glucose level information table 192, to be displayed as illustrated in FIG. 21 in which corresponding elements to those in FIG. 20 are denoted by like reference symbols.

If the comparison button 86 of the graph display screen image 200 is selectively operated through the operation unit 16, then the CPU 11 causes the average graph 201 and the bar graph 202 to be displayed in a reduced scale in the vertical direction to be displayed on the upper side of the graph display region 77 and causes an average graph and a bar graph within the range same as that of the average graph 201 and the bar graph 202 but within an immediately preceding period to be displayed on the lower side of the graph display region 77 in a manner similar to the case where the graph display screen image 90 is displayed when the comparison button 86 of the graph display screen image 70 described hereinabove is selectively operated.

Figure 22:
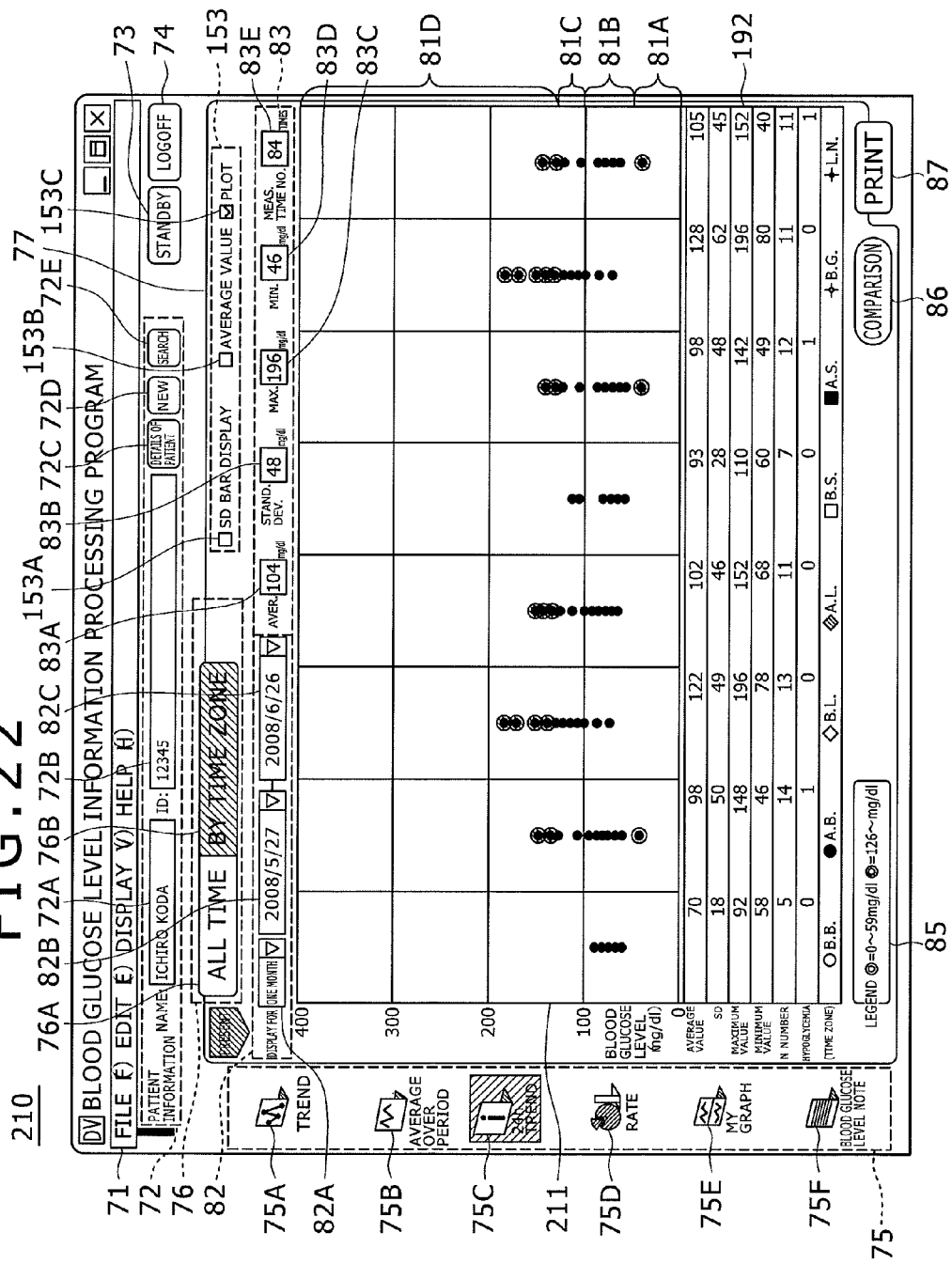
FIG. 22 is a schematic illustration of a configuration of a graph display screen image in which a plot graph for each time slot is displayed.

Meanwhile, if the plot check box 153C of the check box field 153 in the graph display screen image 190 (FIG. 20) is selectively operated through the operation unit 16, then the CPU 11 causes such a graph display screen image 210 as illustrated in FIG. 22 in which corresponding elements to those in FIG. 20 are denoted by like reference symbols to be displayed. At this time, the CPU 11 places a check into the plot check box 153C of the check box field 153 and removes the check of the average value check box 153B. It is to be noted that, while the blood glucose levels used in FIGS. 20 and 22 are actually the same as each other, for the convenience of description, different blood glucose levels are used in FIGS. 20 and 22, and the values of the average graph 191 of FIG. 20, a plot graph 211 of FIG. 22 and the blood glucose level information table 192 are merely an example of such blood glucose levels.

Further, the CPU 11 causes a plot graph 211, wherein the extracted blood glucose levels for one month are sorted for each time slot and plotted, to be displayed in the graph display region 77 of the graph display screen image 210.

With the plot graph 211, in the case where the plotted blood glucose levels range from 0 to 59 [mg/dl] or are higher than 126 [mg/dl] as indicated in the legend display region 85, if the plot points of the plotted blood glucose levels are displayed emphatically, then they can be visually confirmed readily by the doctor.

If the comparison button 86 of the graph display screen image 210 is selectively operated through the operation unit 16, then the CPU 11 causes the plot graph 211 to be displayed in a reduced scale in the vertical direction on the upper side of the graph display region 77 and causes a plot graph (not shown) within the range same as that of the plot graph 211 but within an immediately preceding period to be displayed on the lower side of the graph display region 77 in a manner similar to the case where the graph display screen image 90 is displayed when the comparison button 86 of the graph display screen image 70 described hereinabove is selectively operated.

Figure 23:
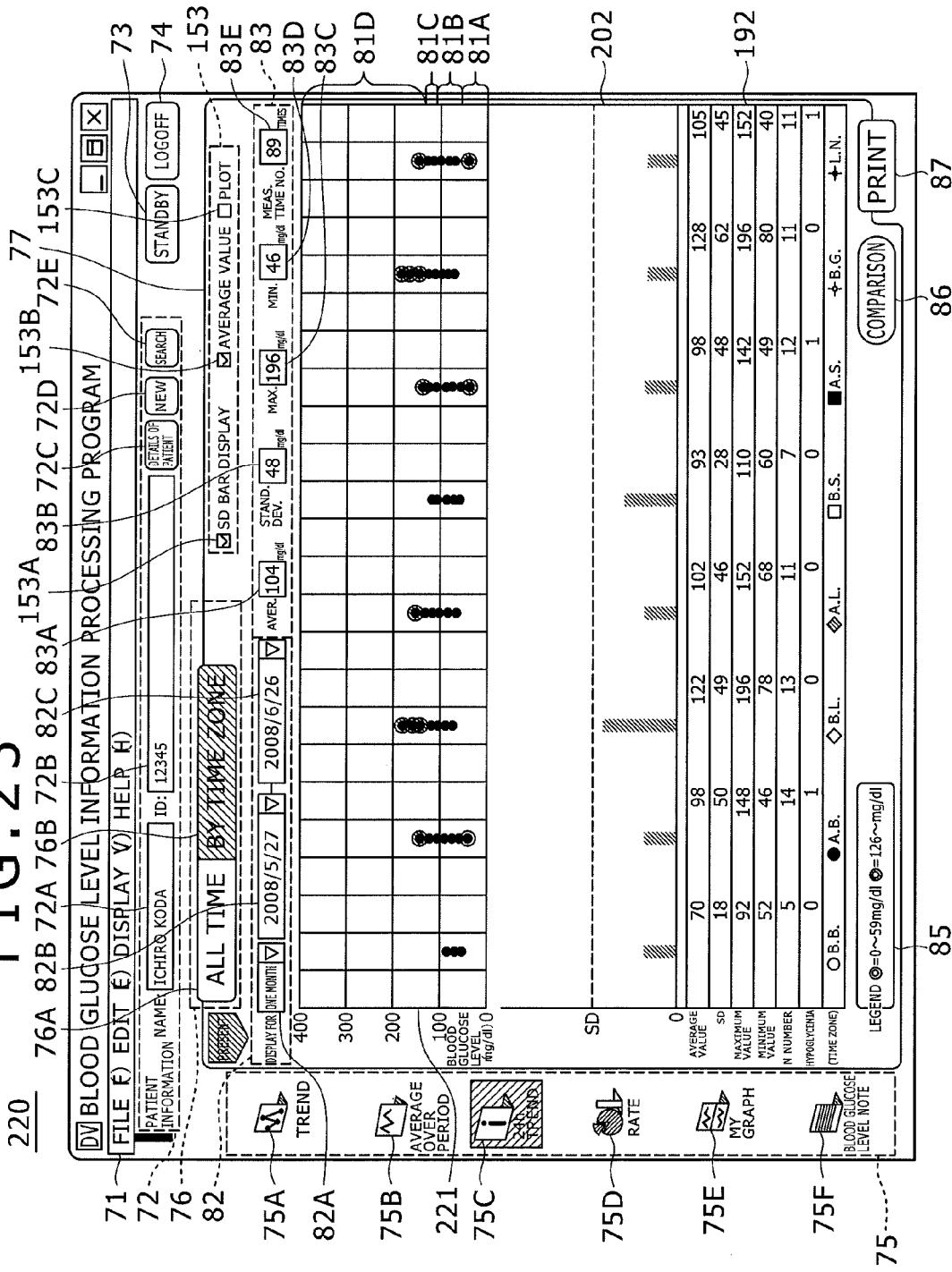
FIG. 23 is a schematic illustration of a configuration of a graph display screen image in which a plot graph and a standard deviation line graph for each time slot are displayed.

If an SD bar display check box 153A of the check box field 153 in the graph display screen image 210 is selectively operated through the operation unit 16, then the CPU 11 causes a graph display screen image 220, in which a bar graph 202 wherein standard deviation values for each time slot indicated as bars is displayed, to be displayed between a plot graph 221 obtained by reducing the plot graph 211 in the vertical direction and the blood glucose level information table 192 as illustrated in FIG. 23 in which corresponding elements to those in FIGS. 21 and 22 are denoted by like reference symbols.

If the comparison button 86 of the graph display screen image 220 is selectively operated through the operation unit 16, then the CPU 11 causes the plot graph 221 and the bar graph 202 to be displayed in a reduced scale in the vertical direction to be displayed on the upper side of the graph display region 77 and causes a plot graph and a bar graph within the range same as that of the plot graph 221 and the bar graph 202 but within an immediately preceding period to be displayed on the lower side of the graph display region 77 in a manner similar to the case where the graph display screen image 90 is displayed when the comparison button 86 of the graph display screen image 70 described hereinabove is selectively operated.

Figure 24:
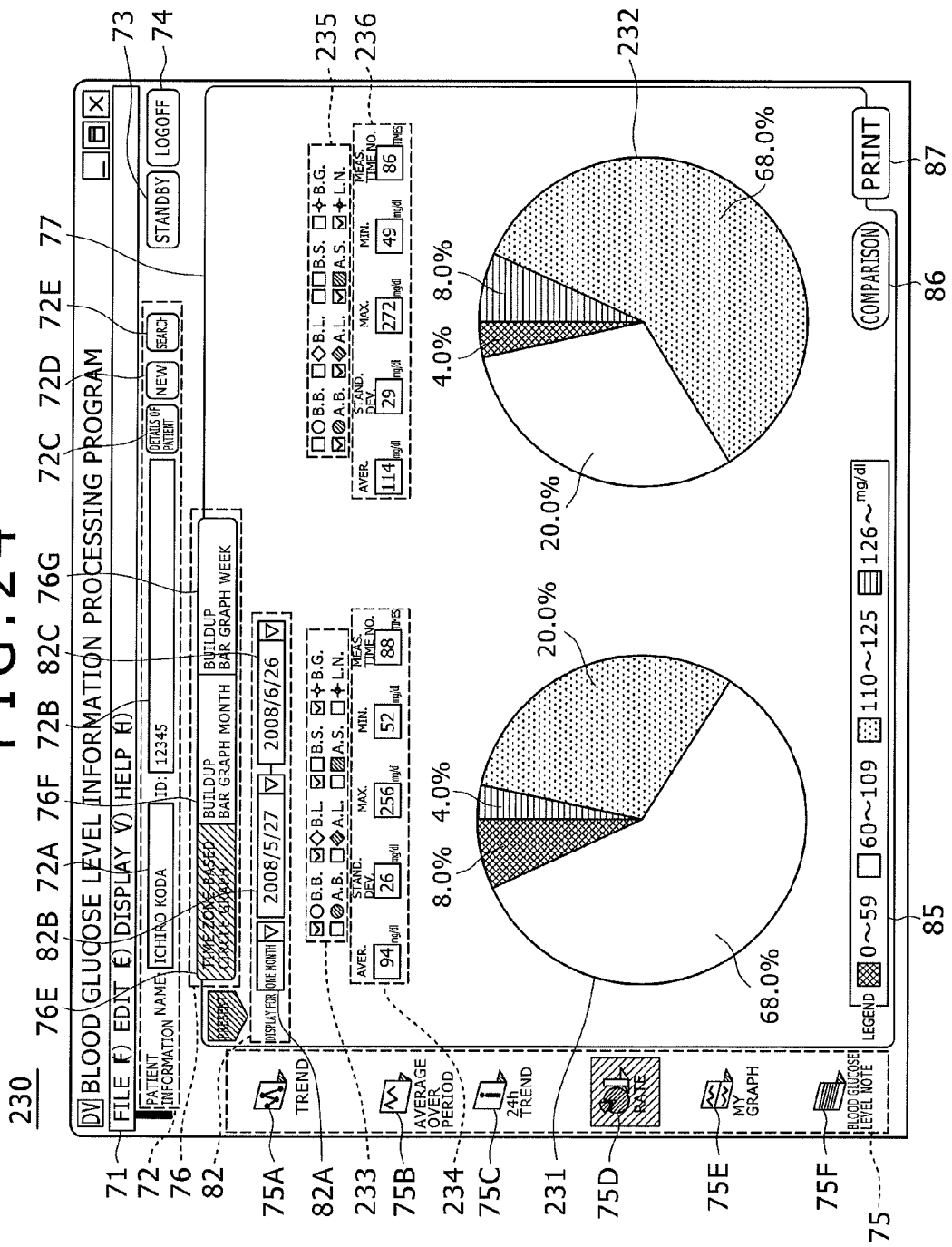
FIG. 24 is a schematic illustration of a configuration of a graph display screen image in which a circle graph is displayed.

If, for example, the rate button 75D of the graph kind selection button display region 75 in the graph display screen image 70 (FIG. 8) is selectively operated through the operation unit 16, then the CPU 11 controls the display unit 15 to display a graph display screen image 230 as illustrated in FIG. 24 in which corresponding elements to those in FIG. 8 are denoted by like reference symbols.

On this graph display screen image 230, a by-time slot (time zone-based) circle graph button 76E, a buildup bar graph month button 76F and a buildup bar graph week button 76G are displayed in the graph type selection button display region 76, and by default, the time zone-based circle graph button 76E is selectively displayed. In this instance, on the graph display screen image 230, two circle graphs 231 and 232 are displayed in a leftwardly and rightwardly juxtaposed relationship with each other in the graph display region 77.

Further, the range selection menu 82A is configured so as to allow selection of, for example, "one month," "two months," "three months" and "six months," and by default, "one month" is selectively displayed.

When the graph display screen image 230 is displayed on the display unit 15, the CPU 11 extracts blood glucose levels within the time slots with regard to which a check is placed in a time slot selection check box 233 (in this instance, "before breakfast," "before lunch," "before supper" and "before going to bed") within the period displayed in the start date display field 82B and the end date display field 82C from the blood glucose level database based on the date/time of measurement and the time slot.

Then, the CPU 11 calculates an average value, a standard deviation value, a maximum value, a minimum value and a data number of the blood glucose levels extracted for each time slot and calculates the rate of the number of data where the blood glucose level ranges from 0 to 59, from 60 to 109, from 110 to 125 and equal to and higher than 126 to the number of data of the extracted blood glucose levels.

The CPU 11 causes the calculated average value, standard deviation value, maximum value, minimum value and data number of the blood glucose levels for each time slot to be displayed in a blood glucose level information table 234 and causes the calculated rate of the blood glucose levels to be displayed as a circle graph 231.

The CPU 11 also extracts blood glucose levels within the time slots with regard to which a check is placed in a time slot selection check box 235 (in this instance, "after breakfast," "after lunch," "after supper" and "late at night") within the period displayed in the start date display field 82B and the end date display field 82C from the blood glucose level database based on the date/time of measurement and the time slot.

Then, the CPU 11 calculates an average value, a standard deviation value, a maximum value, a minimum value and a data number of the extracted blood glucose levels and calculates the rate of the number of data where the blood glucose level ranges from 0 to 59, from 60 to 109, from 110 to 125 and equal to and higher than 126 to the number of data of the extracted blood glucose levels.

Further, the CPU 11 causes the calculated average value, standard deviation value, maximum value, minimum value and data number of the blood glucose levels for each time slot to be displayed in a blood glucose level information table 236 and causes the calculated rate of the blood glucose levels to be displayed as a circle graph 232.

If the comparison button 85 of the graph display screen image 230 is selectively operated through the operation unit 16, then the CPU 11 causes the circle graph 231 and the circle graph 232 to be displayed in a reduced scale on the upper side of the graph display region 77 and causes circle graphs (not shown) within the range same as that of the circle graph 231 and the circle graph 232 but within an immediately preceding period to be displayed on the lower side of the graph display region 77 similarly as in the case where the graph display screen image 90 is displayed when the comparison button 86 of the graph display screen image 70 described above is selectively operated.

Figure 25:
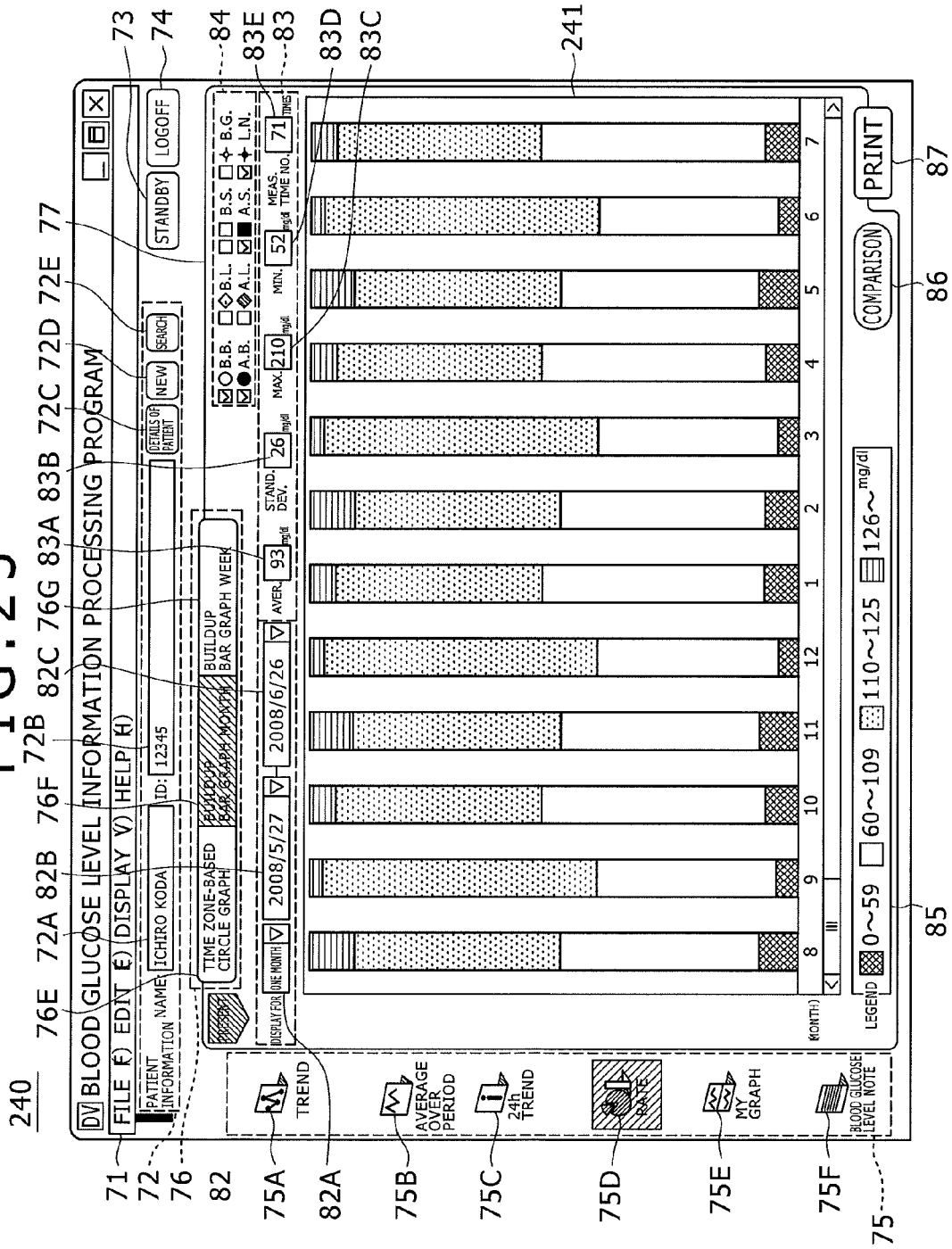
FIG. 25 is a schematic illustration of a configuration of a graph display screen image in which a buildup bar graph for each month is displayed.

On the other hand, if the buildup bar graph month button 76F of the graph type selection button display region 76 on the graph display screen image 230 is selectively operated through the operation unit 16, then the CPU 11 controls the display unit 15 to display such a graph display screen image 240 as illustrated in FIG. 25 in which corresponding elements to those in FIG. 24 are denoted by like reference symbols.

When the graph display screen image 240 is displayed on the display unit 15, the CPU 11 extracts blood glucose levels within the time slots with regard to which a check is placed in a time slot selection check box 84 (in this instance, "before breakfast," "after breakfast," "after supper" and "late at night") within the period displayed in the start date display field 82B and the end date display field 82C from the blood glucose level database based on the date/time of measurement and the time slot.

Then, the CPU 11 calculates an average value, a standard deviation value, a maximum value, a minimum value and a data number of the extracted blood glucose levels and calculates the rate of the number of data where the blood glucose level ranges from 0 to 59, from 60 to 109, from 110 to 125 and equal to and higher than 126 to the number of data for each month of the extracted blood glucose levels.

Then, the CPU 11 causes the calculated average value, standard deviation value, maximum value, minimum value and data number of the calculated blood glucose levels to be displayed in a blood glucose level information display region 83 and causes the calculated rate of the blood glucose levels for each month to be displayed as a bar graph 241.

If the comparison button 86 of the graph display screen image 240 is selectively operated through the operation unit 16, then the CPU 11 causes the bar graph 241 to be displayed in a reduced scale in the vertical direction on the upper side of the graph display region 77 and causes a bar graph within the range same as that of the bar graph 241 but within an immediately preceding period to be displayed on the lower side of the graph display region 77 in a manner similar to the case where the graph display screen image 90 is displayed when the comparison button 86 of the graph display screen image 70 described hereinabove is selectively operated.

Figure 26:
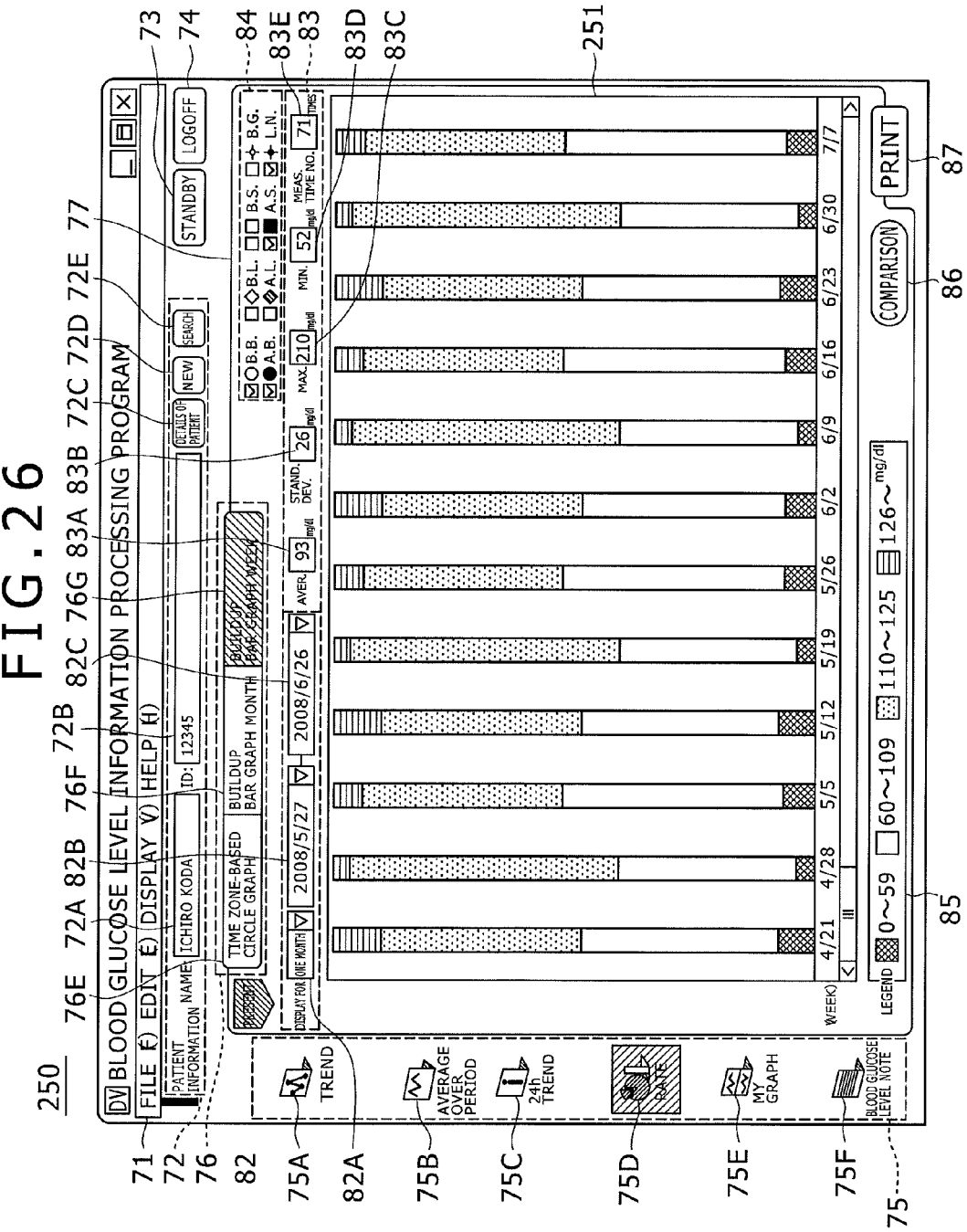
FIG. 26 is a schematic illustration of a configuration of a graph display screen image in which a buildup bar graph for each week is displayed.

On the other hand, if the buildup bar graph week button 76G of the graph type selection button display region 76 on the graph display screen image 230 (FIG. 24) is selectively operated through the operation unit 16, then the CPU 11 controls the display unit 15 to display such a graph display screen image 250 as illustrated in FIG. 26 in which corresponding elements to those in FIG. 24 are denoted by like reference symbols.

The CPU 11 extracts blood glucose levels within the time slots with regard to which a check is placed in the time slot selection check box 84 (in this instance, "before breakfast," "after breakfast," "after supper" and "late at night") within a period displayed by the start date display field 82B and the end date display field 82C, which corresponds to "12 weeks" displayed by default in the range selection menu 82A, from the blood glucose level database based on the date/time of measurement and the time slot. Then, the CPU 11 calculates an average value, a standard deviation value, a maximum value, a minimum value and a data number of the extracted blood glucose levels and calculates the rate of the number of data where the blood glucose level ranges from 0 to 59, from 60 to 109, from 110 to 125 and equal to and higher than 126 to the number of data for each week of the extracted blood glucose levels.

Then, the CPU 11 causes the calculated average value, standard deviation value, maximum value, minimum value and data number of the calculated blood glucose levels to be displayed in the blood glucose level information display region 83 and causes the calculated rate of the blood glucose levels for each week to be displayed as a bar graph 251.

If the comparison button 86 of the graph display screen image 250 is selectively operated through the operation unit 16, then the CPU 11 causes the bar graph 251 to be displayed in a reduced scale in the vertical direction on the upper side of the graph display region 77 and causes a bar graph within the range same as that of the bar graph 251 but within an immediately preceding period to be displayed on the lower side of the graph display region 77 in a manner similar to the case where the graph display screen image 90 is displayed when the comparison button 86 of the graph display screen image 70 described hereinabove is selectively operated.

Figure 27:
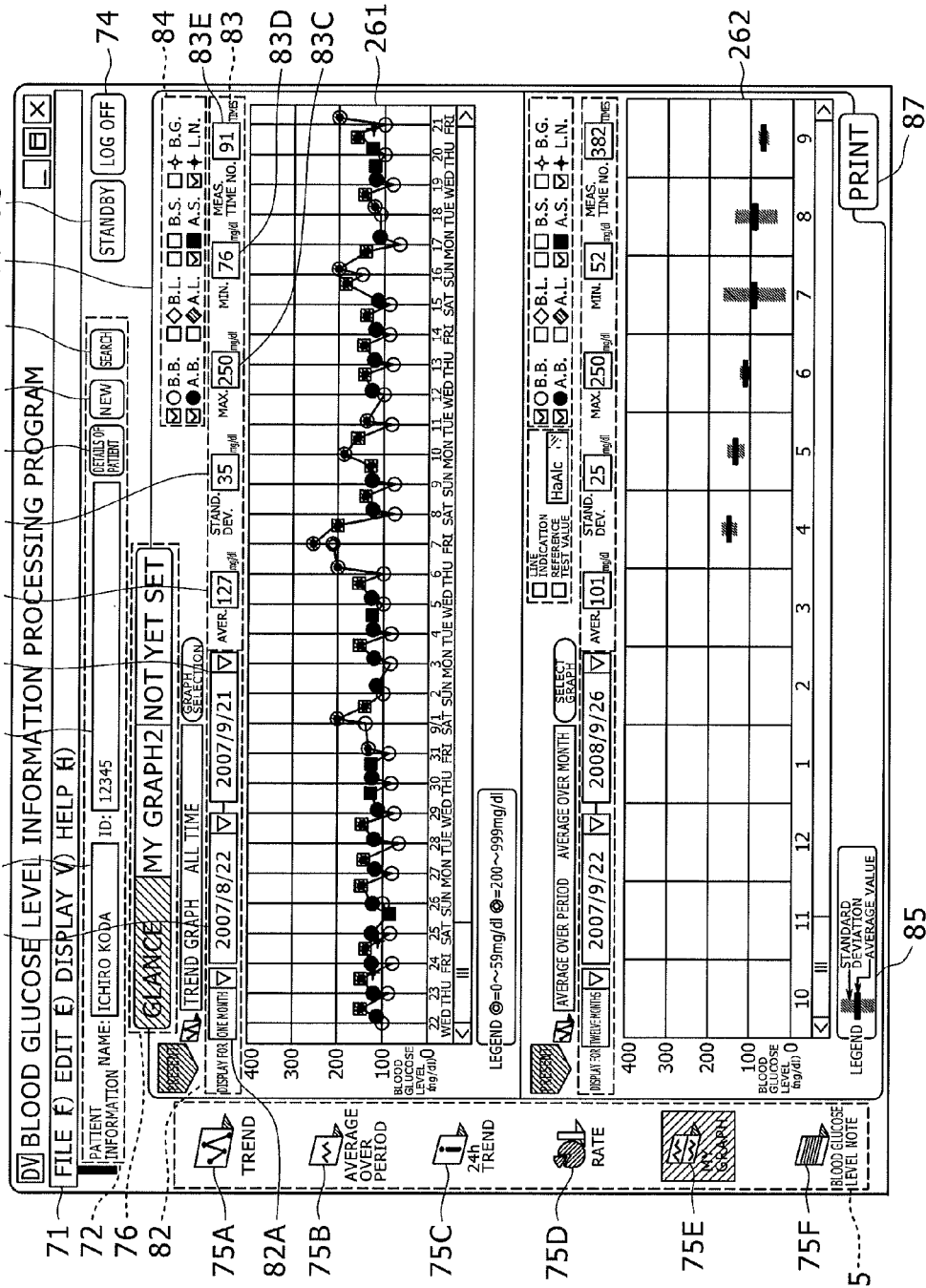
FIG. 27 is a schematic view showing a configuration of a graph display screen image in the case where a My graph button is selected.

If, for example, the My graph button 75E of the graph kind selection button display region 75 in the graph display screen image 70 (FIG. 8) is selectively operated through the operation unit 16, then the CPU 11 controls the display unit 15 to display a graph display screen image 260 as illustrated in FIG. 27 in which corresponding elements to those in FIG. 8 are denoted by like reference symbols.

Here, the graph display screen image 260 allows an arbitrary graph to be displayed, and for example, a line graph 261 corresponding to the line graph 81 shown in FIG. 8 and an average graph 262 corresponding to the average graph 111 shown in FIG. 12 are displayed in the graph display region 77.

Figure 28:
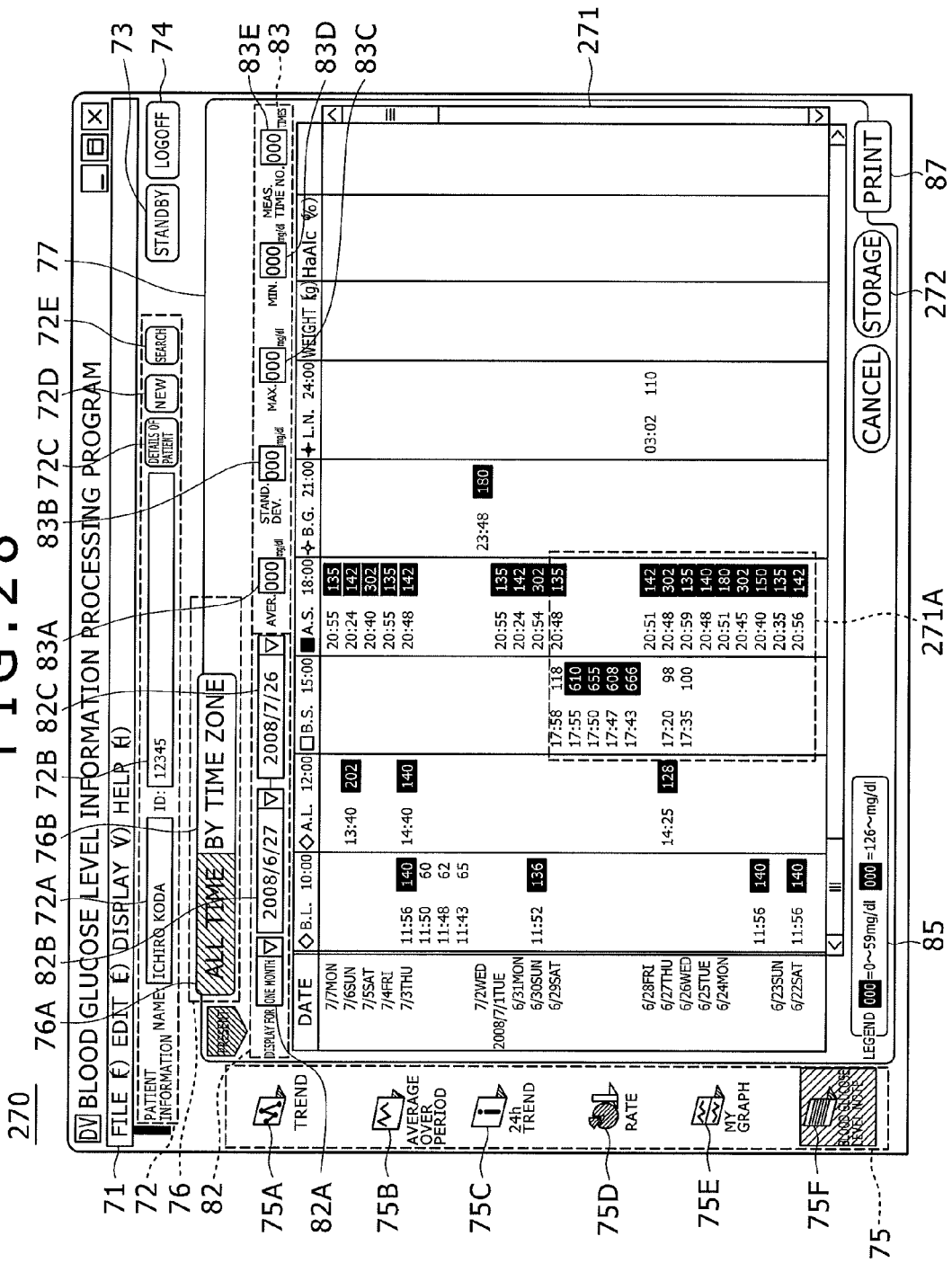
FIG. 28 is a schematic illustration of a configuration of a blood glucose level note display screen image.

For example, if the blood glucose level note button 75F of the graph kind selection button display region 75 on the graph display screen image 70 (FIG. 8) is selectively operated through the operation unit 16, then the CPU 11 causes a blood glucose level table 271, in which the blood glucose levels recorded in the blood glucose level database are displayed in a list together with the measurement time, to be displayed on a blood glucose level note display screen image 270 as illustrated in FIG. 28 in which corresponding elements to those in FIG. 8 are denoted by like reference symbols.

In particular, in the blood glucose level table 271, the axis of ordinate is the date and the axis of abscissa indicates the time slot, and the blood glucose levels are disposed in a matrix together with the measurement time. In the blood glucose level table 271, where the blood glucose level ranges from 0 to 59 [mg/dl] or is equal to or higher than 126 [mg/dl], the blood glucose level is displayed in an inverted form.

The blood glucose level is measured by a patient himself/herself when the patient is, for example, in home or in a company before meal, after meal or the like by means of the blood glucose level measuring device 5 (FIG. 1). Further, the patient may not necessarily take a meal in accordance with the set time slots. Therefore, when the CPU 11 sorts a blood glucose level into a relevant time slot based on the time of measurement of the measurement data measured by the blood glucose level measuring device 5, it may possibly sort the blood glucose level into a time slot different from an actual time slot to produce a blood glucose level database. Further, since some date/time are set by a patient, for example, upon initialization, the blood glucose level measuring device 5 may possibly have wrong date/time set therein.

Therefore, the blood glucose level information processing apparatus 2 is configured so that a blood glucose level database produced by the CPU 11 can be corrected based on a decision of the doctor.

Figure 29:
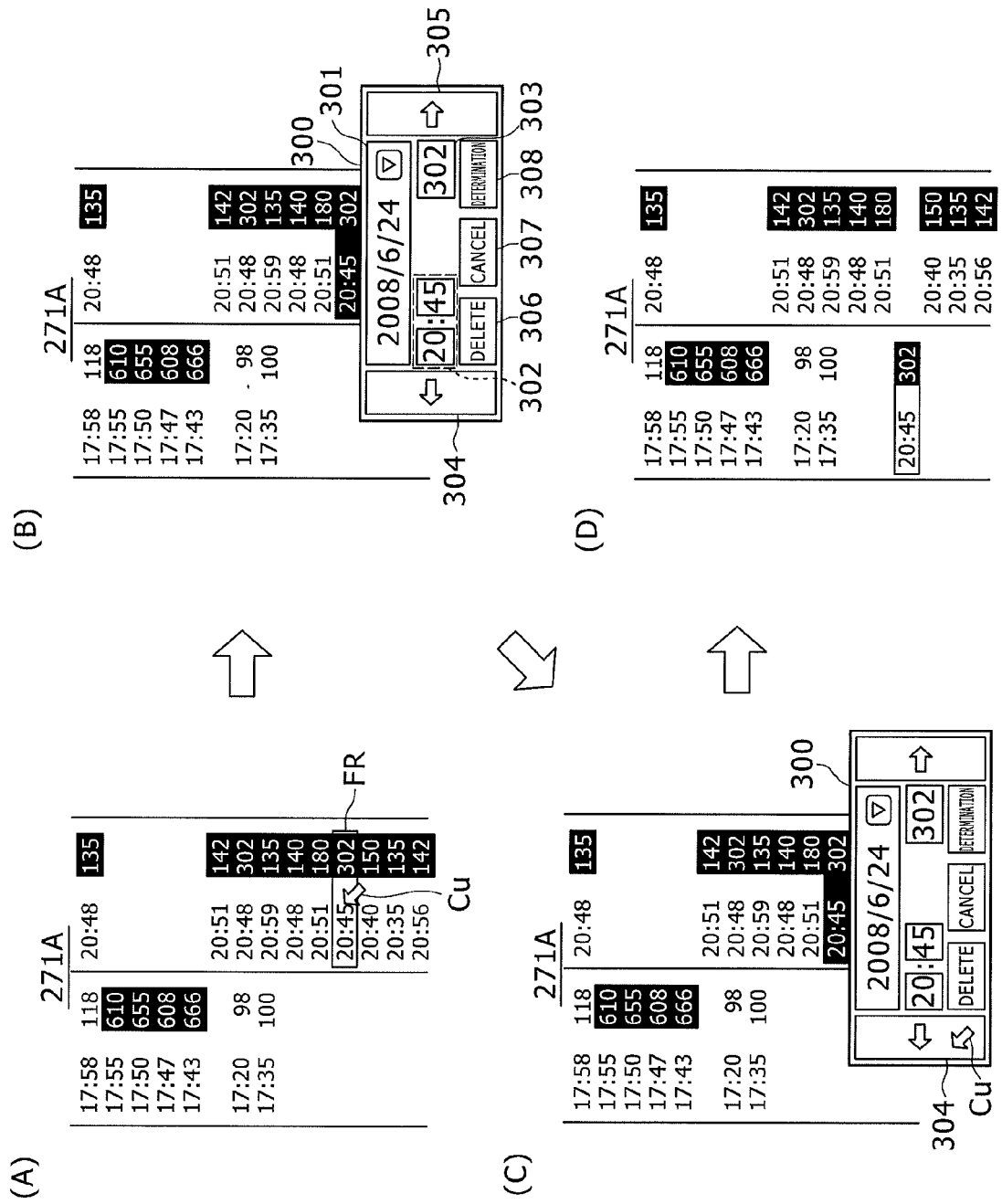
FIG. 29 is a schematic illustration of a manner of alteration of time slots.

In particular, as seen in FIG. 29(A) which illustrates a blood glucose level table part 271A which is part of FIG. 28, if an arbitrary blood glucose level of the blood glucose level table 271 is selected (clicked) by a cursor Cu, then the CPU 11 surrounds the blood glucose level and corresponding measurement time with a selection framework FR so that the doctor visually confirms that the arbitrary blood glucose level is selected.

Then, if it is recognized that, for example, the mouse of the operation unit 16 is double-clicked to make a determination in a state in which a blood glucose level surrounded with the selection framework FR is selected, then the CPU 11 causes the blood glucose level and the measurement time to be displayed in a reverse image while a time slot changing popup menu 300 is displayed in an overlapping relationship with the blood glucose level table 271 just below the blood glucose level as seen in FIG. 29(B).

On this time slot changing popup menu 300, a measurement date display field 301 for displaying the measurement date of a determined blood glucose level, a measurement time display field 302 for displaying measurement time of the blood glucose level, a blood glucose level display field 303 for displaying the blood glucose level, a left button 304 for moving the time slot of the blood glucose level to an immediately preceding time slot, a right button 305 for moving the time slot of the blood glucose level to an immediately succeeding time slot, a delete button 306, a cancel button 307 and a determination button 308 are provided.

If the CPU 11 recognizes that the left button 304 of the time slot changing popup menu 300 is selected through the cursor Cu as indicated by FIG. 29(C), then it moves and displays the selected blood glucose level to and at the left side time slot, that is, an immediately preceding time slot, as seen in FIG. 29(D). At this time, the CPU 11 keeps the blood glucose level whose time slot is moved in the selected state in which the blood glucose level is surrounded with the selection framework FR so that the blood glucose level whose time slot is changed can be found out readily by the doctor.

On the other hand, if the CPU 11 recognizes that the right button 305 of the time slot changing popup menu 300 is selected through the cursor Cu, then it moves and displays the selected blood glucose level to and at the right side time slot, that is, an immediately succeeding time slot.

Furthermore, if the CPU 11 recognizes that the determination button 308 is selected through the cursor Cu after the measurement date display field 301 which is a pull-down menu of the time slot changing popup menu 300 is changed through the operation unit 16, then it moves and displays the selected blood glucose level to and at the changed measurement date.

Further, if the CPU 11 recognizes that the determination button 308 is selected through the cursor Cu after an inputting operation into the measurement time display field 302 of the time slot changing popup menu 300, for example, through the keyboard of the operation unit 16, then the CPU 11 re-sorts the time slot based on the inputted measurement time. Then, the CPU 11 moves and displays the blood glucose level to and at the re-sorted time slot.

In this manner, with the blood glucose level information processing apparatus 2, a time slot, measurement date and measurement time of a blood glucose level measured by the blood glucose level measuring device 5 can be changed by causing the doctor to carry out a predetermined operation for the time slot changing popup menu 300.

And, if a storage button 272 (FIG. 28) is selected through the operation unit 16, then the blood glucose level information processing apparatus 2 updates the blood glucose level database in regard to the updated time slot, measurement date and measurement time of the blood glucose level in order that the updated time slot, measurement date and measurement time may be reflected.

Consequently, the blood glucose level information processing apparatus 2 can change the time slot, measurement date and measurement time of the blood glucose level to such a time slot, measurement date and measurement time as are considered to be appropriate, for example, by a decision of the doctor. Therefore, various graph displays described hereinabove can be carried out using the changed time slot, measurement date and measurement time, and more appropriate decision materials can be provided to the doctor.

The blood glucose level information processing apparatus 2 having the configuration described above acquires measurement data, including the blood glucose level measured by the blood glucose level measuring device 5 and the measurement date/time at which the blood glucose level is measured, through the external connection interface unit 17 and stores such measurement data in the hard disk drive 14 for each patient. The CPU 11 forming a part of the blood glucose level information processing apparatus 2 thus include acquisition means for acquiring the measurement data (e.g., measured blood glucose level and the date/time at which the blood glucose level is measured) and storing such measurement data in the hard disk drive 14 for each patient.

Further, the blood glucose level information processing apparatus 2 sorts each blood glucose level of the measurement data into one of a plurality of time slots based on the date/time of measurement at which the blood glucose level is measured and the time slot table 60 (FIG. 7). Then, the blood glucose level information processing apparatus 2 produces a blood glucose level database wherein the blood glucose level and date/time of measurement of the measurement data and the sorted time slot are associated with each other. The CPU 11 of the blood glucose level information processing apparatus 2 thus operates as a sorting means for sorting the blood glucose level measurement data into different time slots based on the date/time of the blood glucose level measurement and a time slot table which sets forth various time slots. The CPU uses this information to produce a blood glucose level database in which the measured blood glucose level, the date/time of measurement, and the sorted time slot are associated with each other.

If the blood glucose level note button 75F of the graph kind selection button display region 75 on the graph display screen image 70 (FIG. 8) is selectively operated through the operation unit 16, then the blood glucose level information processing apparatus 2 causes the blood glucose level table 271, in which blood glucose levels recorded in the blood glucose level database are displayed in a table together with the measurement time, to be displayed on the blood glucose level note display screen image 270 (FIG. 28).

At this time, if it is recognized that an arbitrary blood glucose level of the blood glucose level table 271 is selectively determined, then the blood glucose level information processing apparatus 2 displays the blood glucose level in a reverse image, and displays the time slot changing popup menu 300 immediately below the blood glucose level. Then, if the left button 304 or the right button 305 is selected, the selected blood glucose level is moved to and displayed at an immediately preceding or immediately succeeding time slot and updates the blood glucose level database so that the blood glucose level is re-sorted into an immediately preceding or immediately succeeding time slot.

Accordingly, since the blood glucose level information processing apparatus 2 can change the time slot of the blood glucose level to that which is considered appropriate, for example, depending upon a decision of the doctor, such various graph displays as described hereinabove can be carried out using the changed time slot. Consequently, a more appropriate decision material can be provided to the doctor.

Further, since the blood glucose level information processing apparatus 2 does not change the measurement time of an arbitrary blood glucose level when the time slot of the blood glucose level is changed, for example, when the graph display screen images 150, 160, 170 and 180 (FIGS. 16 to 19) in which a blood glucose level for each one hour is used are to be displayed, graph display which reflects the measurement time accurately can be carried out.

Furthermore, even if the blood glucose level measuring device 5 is set to wrong time, by changing the measurement date and the measurement time of an arbitrary blood glucose level in response to an operation for the time slot changing popup menu 300, such various graph displays as described above can be carried out using the changed measurement date and measurement time.

Further, in the blood glucose level information processing apparatus 2, the slide bar 88 is provided below the line graph 81 obtained by plotting blood glucose levels, for example, for one month along the time series, for example, on the graph display screen image 70 such that, if the slide bar 88 is moved in parallel, then only the blood glucose levels for one month backdating in response to the amount of movement of the slide bar 88 are plotted on the line graph 81 along the time series.

Accordingly, by changing the period of the blood glucose levels to be plotted on the line graph 81 in response to the amount of movement of the slide bar 88 without changing the range of the blood glucose level, the period of those blood glucose levels to be plotted on the line graph 81 can be changed readily.

Consequently, only by moving the slide bar 88 in parallel, the blood glucose level information processing apparatus 2 can change the period of those blood glucose levels to be plotted at any time in response to the movement of the slide bar 88. Therefore, it is possible to allow the doctor to visually confirm the transition of the blood glucose level continuously for a long period of time.

Further, if the slide bar 88 is moved in parallel, then the blood glucose level information processing apparatus 2 calculates the average value, standard deviation value, maximum value, minimum value and data number of the calculated blood glucose levels plotted on the line graph 81 again backdating in response to the amount of movement of the slide bar 88. Then, the blood glucose level information processing apparatus 2 displays the average value, standard deviation value, maximum value, minimum value and data number in the average value display field 83A, standard deviation value display field 83B, maximum value display field 83C, minimum value display field 83D and measurement time number display field 83E of the blood glucose level information display region 83, respectively.

Consequently, the blood glucose level information processing apparatus 2 can display the average value, standard deviation value, maximum value, minimum value and data number only of the blood glucose levels plotted on the line graph 81 at present in response to the movement of the slide bar 88.

Meanwhile, for example, if the comparison button 86 of the graph display screen image 70 is selectively operated, then the blood glucose level information processing apparatus 2 displays the line graph 81 in a scaled reduced in the vertical direction on the upper side of the graph display region 77 and displays the line graph 92 within the same range as that of the line graph 81 but within an immediately preceding period on the lower side of the graph display region 77.

Accordingly, by only causing the doctor to carry out a simple operation of selecting the comparison button 86, the blood glucose level information processing apparatus 2 can provide, for example, line graphs within the same range but within two successive periods.

Further, by displaying, for example, line graphs within the same range and within two successive periods, it is possible to allow transitions of blood glucose levels within two successive periods to be compared with each other.

With the configuration described above, the blood glucose level information processing apparatus 2 acquires a blood glucose level measured by the blood glucose level measuring device 5 and date/time at which the blood glucose level is measured, sorts such blood glucose levels into a plurality of time slots based on the date/time of measurement, displays, if it recognizes that an arbitrary blood glucose level of the blood glucose level table 271 whose axes are the time slot and the date/time of measurement is selectively determined, the time slot changing popup menu 300, and then moves, if the left button 304 or the right button 305 is selected, the selected blood glucose level to an immediately preceding or immediately succeeding time slot. Consequently, a blood glucose level and blood glucose level information of time slots which are more accurate than ever can be provided.

Further, the blood glucose level information processing apparatus 2 acquires a blood glucose level measured by the blood glucose level measuring device 5 and date/time at which the blood glucose level is measured, provides the slide bar 88 below the line graph 81 formed by plotting blood glucose levels, for example, for one month along the time series, for example, on the graph display screen image 70, and plots, if the slide bar 88 is moved in parallel, only the blood glucose levels, for example, for one month backdating in response to the amount of movement of the slide bar 88 on the line graph 81 along the time series. Consequently, the blood glucose level information processing apparatus 2 can easily provide blood glucose levels and blood glucose level information within a period or range desired by the user without imposing cumbersome operation on the user.

In the embodiment described above, the blood glucose level information processing apparatus 2 and the blood glucose level measuring device 5 are connected by wire connection to each other through the communication module 6 and the optical communication unit. But the apparatus and method are not limited in this regard. For example, the blood glucose level information processing apparatus 2 and the blood glucose level measuring device 5 may be connected to each other by wireless communication. Or, the blood glucose level information processing apparatus 2 and the blood glucose level measuring device 5 may be connected by wire connection through a predetermined cable or the like.

The embodiment of the apparatus and method described above involves the single blood glucose level information processing apparatus 2 which stores and manages measurement data supplied from the blood glucose level measuring device 5. The apparatus and method are not limited in this regard. It is possible, for example, that a plurality of blood glucose level information processing apparatus 2 connected to each other, for example, by an intranet or the like may store and manage measurement data supplied from the blood glucose level measuring device 5. Or, one of a plurality of blood glucose level information processing apparatus 2 may serve as a master apparatus which stores and manages measurement data while the remaining one or ones of the blood glucose level information processing apparatus 2 may temporarily use measurement data by accessing the blood glucose level information processing apparatus 2 which serves as the master apparatus.

Though in the embodiment described above, measurement data supplied from the blood glucose level measuring device 5 is stored in folders for individual patients, the apparatus and method are not limited in that regard. In particular, in such a case that a plurality of blood glucose level measuring devices 5 have individually unique identification numbers set thereto, measurement data may be stored for each of the identification numbers of the blood glucose level measuring devices 5.

In this instance, if the blood glucose level information processing apparatus 2 associates the identification numbers of the blood glucose level measuring devices 5 and the patient names with each other in advance, then if a patient name is selected on the patient search screen image 40 (FIG. 6), the blood glucose level information process described hereinabove can be executed by reading out the measurement data from a folder of the identification number associated with the patient name.

Also, while in the embodiment described above, the CPU 11 carries out the blood glucose level information process described above in accordance with the blood glucose level information processing program stored in the hard disk drive 14 in advance, the apparatus and method are not limited in this regard. The blood glucose level information process described above may otherwise be carried out in accordance with a blood glucose level information processing program installed from a storage medium, a blood glucose level information processing program downloaded from the Internet or a blood glucose level information processing program installed through various other routes. The disclosed blood glucose level information processing program preferably involves a non-transitory computer readable medium storing a blood glucose level information processing program which causes a computer to do that described here.

In the embodiment described above, the information processing apparatus 2 as the blood glucose level information processing apparatus is configured from the external connection interface unit 17 serving as an acquisition unit and the CPU 11 serving as a display control means. However, the blood glucose level information processing apparatus may be configured from an acquisition unit and a display control unit having any of various other configurations.

The embodiment described above involves the blood glucose level information processing apparatus 2 serving as an example of the blood glucose level processing apparatus being configured from the external connection interface unit 17 serving as an acquisition means, the CPU 11 serving as an example of a sorting means which sorts the acquired blood glucose levels into a plurality of respective time slots as described above, the CPU 11 serving as an example of the display control means for controlling the display unit to display blood glucose level graphs as described above, the CPU 11 serving as an example of the changing means for changing a selected blood glucose level to a preceding time slot when a button in the pop-up menu is selected and for changing the selected blood glucose level to the succeeding time slot when another button of the pop-up menu is selected as described above. The CPU 11 also is an example of a calculation means for calculating blood glucose level information relating to the blood glucose levels measured in different ranges of measurement dates as described above, as well as a re-calculation means which re-calculates the blood glucose level information when the date range displayed on the graph changes. But the apparatus is not limited to this as other configurations or arrangements are possible. For example, the blood glucose level information processing apparatus may be configured from an acquisition unit, a sorting unit, a display control unit and a changing unit having any of other various configurations.

The apparatus and method described here are applicable not only, for example, to a personal computer but also to various other electronic apparatus such as a PDA (Personal Digital Assistant) or a portable telephone set.

The detailed description above describes features and aspects of the blood glucose level information processing apparatus, method and program disclosed here. But the invention is not limited to the precise embodiment and variations described. Various changes, modifications and equivalents could be effected by one skilled in the art without departing from the spirit and scope of the invention as defined in the appended claims. It is expressly intended that all such changes, modifications and equivalents which fall within the scope of the claims are embraced by the claims.

What is claimed is:

1. A blood glucose level information processing apparatus comprising:
a processor configured to:
acquire blood glucose levels measured by an external blood glucose level measuring instrument and acquire measurement dates and measurement times at which the blood glucose levels are measured;
sort the acquired measured blood glucose levels into a plurality of time slots based on the acquired measurement dates and measurement times, each time slot encompassing a predetermined time period;

control a display unit to 1) display at least some of the acquired blood glucose levels in a table having one axis representing dates and another axis representing the plural time slots, and to 2) display, upon selecting one of the blood glucose values in a current time slot within the table, a popup menu having one button selectable to direct the selected blood glucose value to be moved from the current time slot to a different time slot preceding the current time slot and an other button selectable to direct the selected blood glucose value to be moved a different time slot succeeding the current time slot; and move the selected blood glucose level to the preceding time slot when the one button of the pop-up menu is selected and move the selected blood glucose level to the succeeding time slot when the other button of the pop-up menu is selected.

2. The blood glucose level information processing apparatus according to claim 1, wherein:

the blood glucose level is displayed in the table together with the measurement date and the measurement time at which the blood glucose level was measured; and the selected blood glucose level is changed to the preceding time slot or the succeeding time slot without changing the measurement time of the selected blood glucose level.

3. The blood glucose level information processing apparatus according to claim 1, wherein:

the display unit is controlled to display, in the popup menu, the measurement date and the measurement time of the selected blood glucose level in addition to the one button and the other button; and the measurement date and the measurement time are changed in response to a predetermined changing operation performed by a user.

4. The blood glucose level information processing apparatus according to claim 2, wherein the display unit is controlled to display the popup menu immediately below the selected blood glucose level.

5. A blood glucose level information processing method comprising:

acquiring blood glucose levels measured by a blood glucose level measuring instrument as well as a measurement date and a measurement time at which each blood glucose level was measured;

sorting the acquired blood glucose levels into a plurality of respective time slots which each include a respective period of time so that acquired blood glucose levels measured during each respective time period are sorted into the respective time slot;

displaying at least some of the acquired blood glucose levels in a table which has one axis representing dates and another axis representing the plural time slots;

displaying a popup menu when one of the blood glucose values displayed in the table in a current time slot is selected, the popup menu including one button selectable to direct the selected blood glucose value to be moved from the current time slot to a different time slot preceding the current time slot and an other button to direct the selected blood glucose value to be moved a different time slot succeeding the current time slot; and moving the selected blood glucose level to the preceding time slot when the one button of the pop-up menu is selected and moving the selected blood glucose level to the succeeding time slot when the other button of the pop-up menu is selected.

6. The blood glucose level information processing method according to claim 5, wherein the displaying of at least some of the acquired blood glucose levels in the table comprises displaying the blood glucose level in the table together with the measurement date and the measurement time at which the blood glucose level was measured, and wherein the moving of the selected blood glucose level comprises moving the selected blood glucose level to the different time slot while still displaying the measurement date and the measurement time at which the selected blood glucose level was measured.

7. A blood glucose level information processing program stored in a non-transitory computer readable medium to cause a computer to:

acquire blood glucose levels measured by a blood glucose level measuring instrument as well as a measurement date and a measurement time at which each blood glucose level was measured;

sort the acquired blood glucose levels into a plurality of respective time slots which each include a respective period of time so that acquired blood glucose levels measured during each respective time period are sorted into the respective time slot;

display at least some of the acquired blood glucose levels in a table which has one axis representing dates and another axis representing the plural time slots;

display a popup menu when one of the blood glucose values displayed in the table in a current time slot is selected, the popup menu including one button selectable to direct the selected blood glucose value to be moved from the current time slot to a different time slot preceding the current time slot and an other button to direct the selected blood glucose value to be moved a different time slot succeeding the current time slot; and move the selected blood glucose level to the preceding time slot when the one button of the pop-up menu is selected and moving the selected blood glucose level to the succeeding time slot when the other button of the pop-up menu is selected.

* * * * *